US008962841B2

(12) United States Patent
Hudlicky et al.

(10) Patent No.: US 8,962,841 B2
(45) Date of Patent: *Feb. 24, 2015

(54) METHODS FOR ONE-POT N-DEMETHYLATION/N-FUNCTIONAL- IZATION OF MORPHINE AND TROPANE ALKALOIDS

(75) Inventors: Tomas Hudlicky, St. Catharines (CA); Robert James Carroll, Herts (GB); Hannes Leisch, Unterach am Attersee (AT); Ales Machara, Brevnov (CZ); Lukas Werner, Kadan (CZ); Mary Ann Endoma-Arias, Quezon (PH)

(73) Assignee: Brock University, St. Catharines, Ontario (CA)

( * ) Notice: Subject to any disclaimer, the term of this patent is extended or adjusted under 35 U.S.C. 154(b) by 402 days.

This patent is subject to a terminal disclaimer.

(21) Appl. No.: 13/178,623

(22) Filed: Jul. 8, 2011

(65) Prior Publication Data

US 2011/0313163 A1 Dec. 22, 2011

Related U.S. Application Data

(63) Continuation-in-part of application No. 11/771,191, filed on Jun. 29, 2007, now Pat. No. 7,999,104.

(51) Int. Cl.
| | | |
|---|---|---|
| *A61K 31/44* | (2006.01) |
| *C07D 471/00* | (2006.01) |
| *C07D 491/00* | (2006.01) |
| *C07D 498/00* | (2006.01) |
| *C07D 513/00* | (2006.01) |
| *C07D 515/00* | (2006.01) |
| *C07D 489/00* | (2006.01) |
| *C07D 489/08* | (2006.01) |
| *C07D 451/06* | (2006.01) |
| *C07D 221/22* | (2006.01) |
| *C07D 489/02* | (2006.01) |
| *C07D 489/12* | (2006.01) |

(52) U.S. Cl.
CPC ............ *C07D 451/06* (2013.01); *C07D 221/22* (2013.01); *C07D 489/02* (2013.01); *C07D 489/08* (2013.01); *C07D 489/12* (2013.01)
USPC ................................ 546/45; 546/46; 514/282

(58) Field of Classification Search
CPC .. C07D 471/00; C07D 491/00; C07D 498/00; C07D 513/00; C07D 515/00; C07D 489/00; C07D 489/08
See application file for complete search history.

(56) References Cited

U.S. PATENT DOCUMENTS

| 4,472,253 A | 9/1984 | Schwartz | |
| 4,613,668 A | 9/1986 | Rice | |
| 6,376,221 B1 * | 4/2002 | Fist et al. ................. 435/118 |
| 6,388,079 B1 | 5/2002 | Wu et al. | |
| 6,399,078 B1 | 6/2002 | Devico et al. | |
| 6,440,688 B1 | 8/2002 | Bruce | |
| 6,790,959 B1 * | 9/2004 | Lin et al. ..................... 546/44 |
| 6,864,370 B1 * | 3/2005 | Lin et al. ..................... 546/44 |
| 7,935,820 B2 | 5/2011 | Carroll et al. | |
| 7,999,104 B2 * | 8/2011 | Carroll et al. .............. 546/45 |
| 8,318,937 B2 * | 11/2012 | Mitchell et al. ............. 546/45 |
| 8,431,701 B2 * | 4/2013 | Hudson et al. .............. 546/44 |
| 8,436,174 B2 * | 5/2013 | Cantrell et al. ............. 546/45 |

FOREIGN PATENT DOCUMENTS

| CA | 1244825 | 11/1988 |
| WO | 98/05667 | 2/1998 |
| WO | 01/34608 | 5/2001 |
| WO | WO 2004/108090 A2 * | 12/2004 |
| WO | WO 2004108090 A2 * | 12/2004 |
| WO | 2005/047291 | 5/2005 |
| WO | 2005/113557 | 12/2005 |
| WO | 2006/104656 | 10/2006 |
| WO | 2011/032214 A1 | 3/2011 |

OTHER PUBLICATIONS

Johnstone, RA. et al. Heterogeneous Catalytic Transfer Hydrogenation and Its Relation to Other Methods for Reduction of Organic Compounds. Chem. Rev. 1985, vol. 85, p. 141, C1.*
Birch, AJ. et al. Lateral Control of Skeletal Rearrangement by Complexation of Thebaine with Fe(CO)3. Tetrahedron Letters. 1985, vol. 26, p. 502, lines 1-7.*
Birch, AJ. et al. Lateral Control of Skeletal Rearrangement by Complexation of Thebaine with Fe(CO)3. Tetrahedron Letters. 1985, vol. 26, p. 502.*
Johnstone, RA. et al. Heterogeneous Catalytic Transfer Hydrogenation and Its Relation to Other Methods for Reduction of Organic Compounds. Chem. Rev. 1985, vol. 85, p. 141.*
Dorwold, FZ. Side Reactions in Organic Synthesis. Wiley. 2005, preface.*
Van Santen, RA. et al. Catalysis. Elsevier. 2000, p. 290.*
Sugi, Yoshihiro; Hanaoka, Taka-Aki; Takeuchi, Kazuhiko; Matsuzaki, Hiroki Watanabe; Bando, Ken-Ichiro, "Dealkylation of N,N-dialkylanilines over transition metal catalysts in the presence of ammonia, water and hydrogen", Applied Catalysis A.: General, 103 (1993), 43-53.
Goo, Yukon; Shi, Hongmei; Huo, Shuying; Shen, Shigang, "Kinetics and mechanism of oxidation of N-methylethylamine by bis(hydrogenperiodato)argentate(III) complex anion", Transition Met Chem (2011), 36:59-64.
Suzuki, M., et al. "Synthesis and evaluation of novel 2-oxo-1,2-dihydro-3-quinolinecarboxamide derivatives as potent and selective serotonin 5-HT4 receptor agonists." Chem Pharm Bull (Tokyo). Jan. 2001;49(1):29-39.

(Continued)

*Primary Examiner* — Rita Desai
*Assistant Examiner* — Ben S Michelson
(74) *Attorney, Agent, or Firm* — Dann, Dorfman, Herrell and Skillman; Patrick J. Hagan

(57) ABSTRACT

The present invention provides a method for the N-demethylation and N-functionalization of an N-methylated heterocycle such as a morphine alkaloid or tropane alkaloid. The method comprises reacting the heterocycle with an functionalization agent in the presence of a transition metal catalyst in air or in the presence of an oxidant.

36 Claims, 1 Drawing Sheet

(56) References Cited

OTHER PUBLICATIONS

Lee, S., et al. "Preparation of N-alkylnorpavines via competitive N-dealkylation of quaternary pavines." Heterocycles. 1996;43(7):1403-1414.

Senokuchi, K., et al. "Synthesis and biological evaluation of (+)-epibatidine and the congeners." Synlett. May 1994; 343-344.

Gerszberg, S., et al. "Bis-dealkylation of Quaternary Ammonium Salts." Tetrahedron Letters. 1973;15:1269-1272.

Iijima, I., et al. "Studies in the (+) Morphinan series I. An alternate conversion of (+)-dihydrocodeinone into (+)-codeine." Heterocycles, 1997;6:1157-1165.

Ripper, J.A., et al. "Photochemical N-demethylation of alkaloids." Bioorg Med Chem Lett. Feb. 26, 2001;11(4):443-5.

* cited by examiner

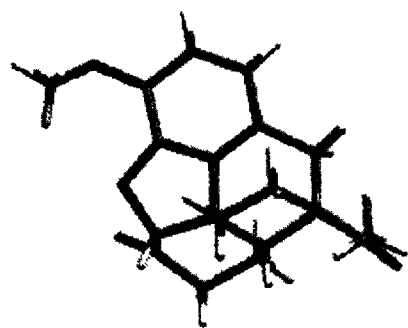

METHODS FOR ONE-POT N-DEMETHYLATION/N-FUNCTIONALIZATION OF MORPHINE AND TROPANE ALKALOIDS

CROSS-REFERENCE TO RELATED APPLICATIONS

The present application is a continuation-in-part of co-pending U.S. patent application Ser. No. 11/771,191 filed on Jun. 29, 2007, the contents of which are incorporated herein by reference in their entirety.

FIELD OF THE INVENTION

The present invention relates to methods for N-demethylation and N-functionalization of various N-heterocyclic compounds, in particular morphine and tropane alkaloids.

BACKGROUND OF THE INVENTION

The semisynthesis of morphine-derived antagonists, such as naloxone, nalbuphone, naltrexone and buprenorphine (see Scheme 1), and other medicinally significant compounds, from opium-derived natural products traditionally involves standard procedures for demethylation followed by subsequent procedures such as oxidation for the introduction of a C-14 hydroxyl group.

Natural opiate alkoloids ⟹ Semisynthetic pharmaceuticals

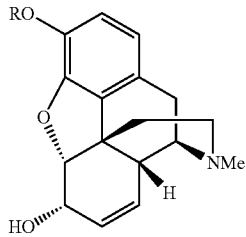

morphine, R = H
codeine, R = Me

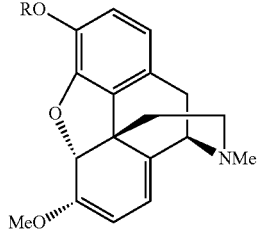

thebaine, R = Me
oripavine, R = H

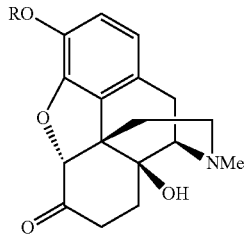

oxycodone, R = Me
oxymorphone, R = H

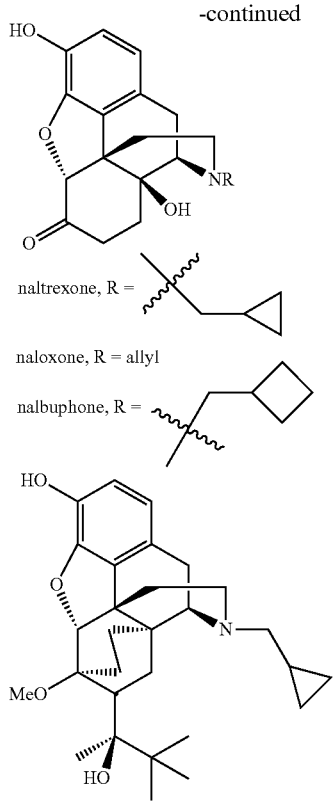

naltrexone, R =
naloxone, R = allyl
nalbuphone, R = buprenorphine

The challenge rests in the formal exchange of the N-methyl group of natural opiates for other functional groups, such as the N-cyclopropylmethyl, N-allyl, or N-cyclobutylmethyl functionality found in naltrexone, naloxone, nalbuphone and buprenorphine. The N-demethylation protocols previously reported include the von Braun reaction employing cyanogen bromide (Von Braun, *J. Chem. Ber.* 1980, 33, 1438), chloroformate reagents (Cooley, J. H.; Evain, E. J. *Synthesis* 1989, 1; Olofson, R. A. et al. *J. Org. Chem.* 1984, 49, 2081), photochemical methods (Ripper, J. A., et al. *Biorg. & Med. Chem. Lett.* 2001, 11, 443-445), demethylation of N-oxides [Polonovski reaction: (a) Kok, G. et al. *Adv. Synth. Catal.* 2009, 351, 283; (b) Dong, Z. et al. *J. Org. Chem.* 2007, 72, 9881; (c) Smith, C. et al. PCT Patent Application Publication No. WO 2005/028483], as well as microbial [(a) Madyashtha, K. M. et al. *Proc. Indian Acad. Sci.* 1984, 106, 1203; (b) Madyastha, K. M. et al. *J. Chem. Soc. Perkin Trans.* 1, 1994, 911] and enzymatic (Chaudhary, V. et al. *Collect. Czech. Chem. Commun.* 2009, 74, 1179) methods. The disadvantages of these methods are that the reagents are highly toxic (cyanogen bromide and ethylchloroformate) or proceed in poor yields (Polonovski and enzymatic methods) requiring significant purification of the desired secondary amine. The secondary amines are then converted to the corresponding products by alkylation.

Therefore any method that avoids these standard procedures may hold immense commercial potential for the production of morphine-derived alkaloids, such as naloxone, naltrexone, nalbuphone, buprenorphine and other medicinally significant compounds.

Current methods for N-demethylation of morphine alkaloids are time consuming, expensive and hazardous. Thus there was an unmet need for improvement in such methods.

Furthermore, there is an increasing demand that production methods be environmentally friendly.

SUMMARY OF THE INVENTION

The present invention provides a one-pot method for N-demethylation and functionalization of N-methylated compounds, particularly morphine alkaloids and their derivatives or tropane alkaloids and their derivatives. Thus, the present invention elucidates conditions for a one-pot oxidative N-demethylation and N-functionalization of morphine and tropane alkaloids that is performed at lower temperatures than prior art methods, is cost effective and safe.

The present invention therefore includes a method for the N-demethylation and functionalization of N-methylated heterocycles comprising reacting an N-methylated heterocycle with a functionalization agent in the presence of a transition metal catalyst. In a further embodiment, the method further comprises reacting the N-methylated heterocycle with the functionalization agent in the presence of a transition metal catalyst and an oxidant.

In one embodiment of the invention, the N-methylated compound is a morphine alkaloid. Accordingly, the present application includes a method of preparing a compound of Formula I:

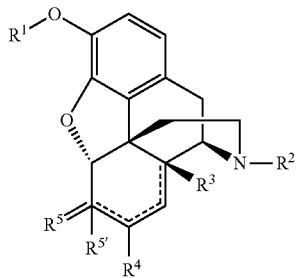

(I)

comprising reacting a compound of Formula II:

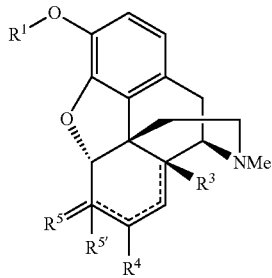

(II)

in the presence of a transition metal catalyst and a compound of Formula III or IV:

 (III)

 (IV)

under conditions to provide the compound of Formula I, wherein, $R^1$ is selected from H, $C_{1-10}$alkyl, $C(O)C_{1-10}$alkyl, $C(O)OC_{1-10}$alkyl and $PG^1$;

$R^2$ is selected from $C(O)R^6$, $C(O)OR^6$, $S(O)R^6$, $SO_2R^6$, $P(O)R^6R^{6'}$, $P(O)(OR^6)R^{6'}$, $P(O)(OR^6)(OR^{6'})$, $C(O)NR^6R^{6'}$ and $C(O)SR^6$;

$R^3$ is selected from H, OH, $OC_{1-10}$alkyl, $OC(O)C_{1-10}$alkyl, $OC(O)OC_{1-10}$alkyl and $OPG^2$ or $R^3$ is not present when the carbon atom to which it is attached is $sp^2$ hybridized, or $R^3$ and $R^{5'}$ form a $CH_2$—$CH_2$ linker between the carbon atoms to which they are attached;

$R^4$ is selected from H, $C_{1-10}$alkyl, $C(O)C_{1-10}$alkyl, hydroxyl-substituted $C_{1-10}$alkyl, and $PG^3$-O-substituted $C_{1-10}$alkyl;

$R^5$ is selected from OH, $OC_{1-10}$alkyl, $OC(O)C_{1-10}$alkyl, $OC(O)OC_{1-10}$alkyl and $OPG^4$ when the ⸗ to which it is attached is a single bond, or $R^5$ is O when the ⸗ to which it is attached is a double bond, $R^{5'}$ is either not present or $R^{5'}$ and $R^3$ form a $CH_2$—$CH_2$ linker between the carbon atoms to which they are attached, only when $R^5$ ⸗ is $R^5$— and the carbon to which it is attached is $sp^3$ hybridized;

$R^6$ and $R^{6'}$ are independently selected from $C_{3-10}$cycloalkyl, $C_{3-10}$heterocycloalkyl, $C_{3-10}$cycloalkenyl, $C_{1-20}$alkyl, $C_{2-20}$alkenyl, $C_{2-20}$alkynyl, $C_{6-10}$aryl and $C_{5-10}$heteroaryl, each of the latter eight groups being unsubstituted or substituted with one or more substituents independently selected from $R^7$, $OR^8$, $SiR^7R^{7'}R^8$, $NR^8R^{8'}$, $SR^8$, $S(O)R^7$, $SO_2R^7$, halo, CN and $NO_2$;

$R^7$ and $R^{7'}$ are independently selected from $C_{1-6}$alkyl, $C_{6-10}$aryl and $C_{1-6}$alkylene$C_{6-10}$aryl;

$R^8$ and $R^{8'}$ are independently selected from H, $PG^5$, $C_{1-6}$alkyl, $C_{6-10}$aryl and $C_{1-6}$alkylene$C_{6-10}$aryl;

⸗ represents a single or double bond, provided that two double bonds are not adjacent to each other;

$PG^1$, $PG^2$, $PG^3$, $PG^4$ and $PG^5$ are independently, a protecting group that is removable after the preparation of the compound of Formula I; and LG is a leaving group, wherein, when (a) $R^1$, $R^8$ and/or $R^{8'}$ are H; (b) $R^3$ and/or $R^5$ is OH; and/or (c) $R^4$ is hydroxyl-substituted $C_{1-10}$alkyl, the method further comprises removal of any $R^2$ group in $R^1$, $R^8$, $R^{8'}$, $R^3$, $R^5$ and/or $R^4$.

In an embodiment of the invention, the method of preparing the compound of Formula I further comprises reacting the compound of Formula II with a compound of Formula III or IV, in the presence of a transition metal catalyst and an oxidant.

In an embodiment, the compounds of Formula II are selected from thebaine, oripavine, 14-hydroxycodeinone, 14-hydroxymorphinone, morphine, codeine, hydromorphone, hydrocodone, oxymorphone, oxycodone, hydromorphol, oxymorphol and [5α,7α]-(1,1-dimethylethyl)-4,5-epoxy-18,19-dihydro-3,6-dimethoxy-α,17-dimethyl-6,14-ethenomorphinan-7-methanol. In a particular embodiment of this aspect the present invention there is provided a one-pot method for N-demethylation and subsequent functionalization of hydrocodone. In another particular aspect of the present invention, there is provided a one-pot method for the N-demethylation and subsequent functionalization of [5α,7α]-(1,1-dimethylethyl)-4,5-epoxy-18,19-dihydro-3,6-dimethoxy-α,17-dimethyl-6,14-ethenomorphinan-7-methanol, for example for the preparation of buprenorphine. In another particular aspect of the present invention, there is provided a one-pot method for the N-demethylation and subsequent functionalization of oxymorphone, for example for the preparation of naltrexone, nalbuphone or naloxone.

In another embodiment of the invention, the N-methylated compound is a tropane alkaloid. Accordingly, the present invention includes a method of preparing a N—$R^2$-functionalized tropane alkaloid comprising reacting an N-methyl tropane alkaloid in the presence of a transition metal catalyst and a compound of Formula III or IV:

$$R^2\text{-LG} \tag{III}$$

$$R^6=C=O \tag{IV}$$

wherein,
$R^2$ is selected from $C(O)R^6$, $C(O)OR^6$, $S(O)R^6$, $SO_2R^6$, $P(O)R^6R^{6'}$, $P(O)(OR^6)R^{6'}$, $P(O)(OR^6)(OR^{6'})$, $C(O)NR^6R^{6'}$ and $C(O)SR^6$, $R^6$ and $R^{6'}$ are independently selected from $C_{3-10}$cycloalkyl, $C_{3-10}$heterocycloalkyl, $C_{3-10}$cycloalkenyl, $C_{1-20}$alkyl, $C_{2-20}$alkenyl, $C_{2-20}$alkynyl, $C_{6-10}$aryl and $C_{5-10}$heteroaryl, each of the latter eight groups being unsubstituted or substituted with one or more substituents independently selected from $R^7$, $OR^8$, $SiR^7R^{7'}R^8$, $NR^8R^{8'}$, $SR^8$, $S(O)R^7$, $SO_2R^7$, halo, CN and $NO_2$;

$R^7$ and $R^{7'}$ are independently selected from $C_{1-6}$alkyl, $C_{6-10}$aryl and $C_{1-6}$alkyleneC$_{6-10}$aryl;

$R^8$ and $R^{8'}$ are independently selected from H, $PG^5$, $C_{1-6}$alkyl, $C_{6-10}$aryl and $C_{1-6}$alkyleneC$_{6-10}$aryl;

$PG^5$ is a protecting group that is removable after the preparation of the N—$R^2$-functionalized tropane alkaloid; and LG is a leaving group,
wherein, when $R^8$ and/or $R^{8'}$ are H; the method further comprises removal of any $R^2$ group in $R^8$ and/or $R^{8'}$.

In an embodiment of the invention, the method of preparing a N—$R^2$-functionalized tropane alkaloid further comprises reacting a N-methyl tropane alkaloid with a compound of Formula III or IV, in the presence of a transition metal catalyst and an oxidant.

In an embodiment of the invention, the N-methyl tropane alkaloid is selected from tropinone, tropane, tropine, atropine, cocaine or any other bicyclo-[3.2.1]-azabicyclic methylamine.

In one embodiment of the invention, the compound of Formula III is an acylating agent. In another embodiment, the acylating agent is an anhydride. Suitable anhydrides include, but are not limited to acetic anhydride, iso-butyric anhydride, n-propanoic anhydride, decanoic anhydride, dodecanoic anhydride, cyclopropylcarbonyl anhydride, cyclobutylcarbonyl anhydride, allylcarbonyl anhydride and anhydrides derived from $C_{1-19}$ carboxylic acids and mixed anhydrides derived therefrom.

In another embodiment of the invention, the acylating agent is a dicarbonate. Suitable dicarbonates include carbonates derived from $C_{1-19}$ alcohols, dimethyl dicarbonate, di-tert-amyl dicarbonate, di-tent-butyl dicarbonate, diallyl pyrocarbonate, dibenzyl dicarbonate, diethyl pyrocarbonate, dimethyl dicarbonate, erythritol bis(carbonate) and mixed carbonates derived thereof.

In yet another aspect of the present invention there is provided a one-pot method for N-demethylation and subsequent carboxylation of morphine or tropane alkaloids and their derivatives to the corresponding carbamates. In this embodiment, the compound of Formula III is suitably a dicarbamic anhydride such as N,N'-dimethylcarbamic anhydride, N,N'-diethylcarbamic anhydride, diphenylcarbamic acid anhydride, N,N'-diphenylcarbonic acid anhydride, N,N'-diphenyldicarbonic diamide, N,N'-(oxydicarbonyl)bisglycine dimethylester, pyrrole-1-carboxylic anhydride or a mixture thereof.

In an embodiment of the invention, the catalyst is a transition metal catalyst selected from the group consisting of $Pd(OAc)_2$, $PdCl_2$, $PdCl_2(PPh_3)_4$, $PdBr_2$, $Pd(acac)_2$, $Pd_2(dba)_3$, $Pd(dba)_2$, $Pd(PPh_3)_4$, or is a transition metal catalyst wherein the active metal is selected from W, V, Cu, Fe, Ru, Co, Rh, Ir, Ni, Pd, Pt, Ge, Sn, Os, Cu, Ag, Au and Pb, and mixtures thereof.

In one embodiment, the method comprises the steps of treating the N-methylated compound with palladium, at least one anhydride but without any added solvent. In another embodiment the palladium source is one of $Pd(OAc)_2$ or $PdCl_2$ and the anhydride is acetic anhydride. In another embodiment the palladium source is $Pd(OAc)_2$.

In another embodiment, the method comprises the step of treating the N-methylated compound with a catalyst, at least one solvent and at least one dicarbonate.

The present invention also includes a method for the preparation of naltrexone or nalbuphone from a compound of Formula I(a):

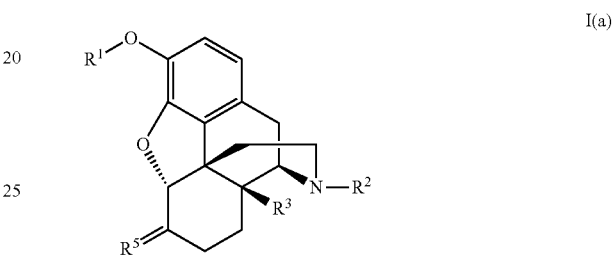

wherein $R^1$ is H, $R^3$ is OH, $=\!=$ is a double bond, $R^5$ is O and $R^2$ is C(O)cyclopropyl or C(O)cyclobutyl, prepared using the method of the invention, comprising:

(a) treating the compound of Formula I(a) with a reducing agent under conditions to provide naltrexone or nalbuphone.

The present invention also includes a method for the preparation of naltrexone, nalbuphone or naloxone from a compound of Formula I(a):

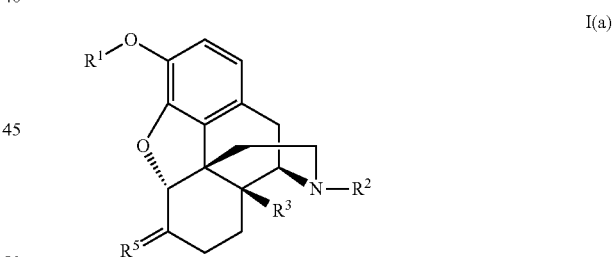

wherein $R^1$ is H, $R^3$ is OH, $=\!=$ is a double bond, $R^5$ is O, $R^2$ is $C(O)R^6$, $R^6$ is selected from $C_{3-10}$cycloalkyl, $C_{3-10}$heterocycloalkyl, $C_{3-10}$cycloalkenyl, $C_{1-20}$alkyl, $C_{2-20}$alkenyl, $C_{2-20}$alkynyl, $C_{6-10}$aryl and $C_{5-10}$heteroaryl, each of the latter eight groups being unsubstituted or substituted with one or more substituents independently selected from $R^7$, $OR^8$, $SiR^7R^{7'}R^8$, $NR^8R^{8'}$, $SR^8$, $S(O)R^7$, $SO_2R^7$, halo, CN and $NO_2$;

$R^7$ and $R^{7'}$ are independently selected from $C_{1-6}$alkyl, $C_{6-10}$aryl and $C_{1-6}$alkyleneC$_{6-10}$aryl; and $R^8$ and $R^{8'}$ are independently selected from H, $C_{1-6}$alkyl, $C_{6-10}$aryl and $C_{1-6}$alkyleneC$_{6-10}$aryl, prepared using the method of the invention, the method comprising (a) treating the compound of Formula I(a) under deacylating conditions followed by an alkylating reagent of the formula cyclopropyl-CH$_2$-LG, cyclobutyl-CH$_2$-LG or CH$_2$=CH—CH$_2$-LG, wherein LG is a leaving group, under conditions to provide naltrexone, nalbuphone or naloxone, respectively.

The present invention also includes a method for the preparing of buprenorphine from a compound of the Formula I(e):

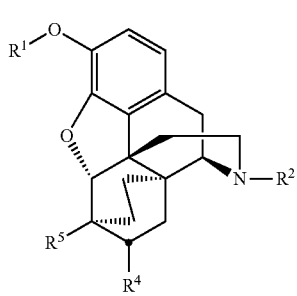

I(e)

wherein R$^1$ is H, R$^4$ is C(O)Me or C(Me)(OH)(t-butyl), R$^5$ is OMe and R$^2$ is C(O)cyclopropyl, prepared using the method the invention, comprising either:
(a) treating the compound of Formula I(e) with a reducing agent under conditions to provide buprenorphine; or
(b) treating the compound of Formula I(e) under deacylating conditions followed by an alkylating reagent of the formula cyclopropyl-CH$_2$-LG, wherein LG is a leaving group, under conditions to provide buprenorphine.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from this detailed description.

BRIEF DESCRIPTION OF THE DRAWINGS

These and other features of the invention will become more apparent from the following description in which reference is made to the appended drawings wherein:

FIG. 1 shows an X-ray structure for N-acetylhydrocodone.

DETAILED DESCRIPTION

I. Definitions

Unless otherwise indicated, the definitions and embodiments described in this and other sections are intended to be applicable to all embodiments and aspects of the application herein described for which they are suitable as would be understood by a person skilled in the art.

As used in this application, the singular forms "a", "an" and "the" include plural references unless the content clearly dictates otherwise. For example, an embodiment including "a catalyst" should be understood to present certain aspects with one catalyst, or two or more additional catalysts.

In embodiments comprising an "additional" or "second" component, such as an additional or second catalyst, the second component as used herein is chemically different from the other components or first component. A "third" component is different from the other, first, and second components, and further enumerated or "additional" components are similarly different.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

In embodiments of the application, the compounds described herein have at least one asymmetric centre. Where compounds possess more than one asymmetric centre, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (e.g. less than 50%, suitably less than 20%, suitably less than 10%, more suitably less than 5%) of compounds having alternate stereochemistry.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "alkyl" as used herein, whether it is used alone or as part of another group, means straight or branched chain, saturated alkyl groups. The term C$_{1-6}$alkyl means an alkyl group having 1, 2, 3, 4, 5, or 6 carbon atoms. The term C$_{1-20}$alkyl means an alkyl group having 1, 2, 3, 4, 5, 6, 7, 8, 9, 10, 11, 12, 13, 14, 15, 16, 17, 18, 19 or 20 carbon atoms. It is an embodiment of the application that, in the alkyl groups, one or more, including all, of the hydrogen atoms are optionally replaced with F or $^2$H and thus include, for example trifluoromethyl, pentafluoroethyl and the like.

The term "alkenyl" as used herein, whether it is used alone or as part of another group, means straight or branched chain, unsaturated alkenyl groups. The term C$_{2-6}$alkenyl means an alkenyl group having 2, 3, 4, 5, or 6 carbon atoms and at least one double bond. The term C$_{1-20}$alkenyl means an alkenyl group having 2, 3, 4, 5, 6, 7, 8, 9, 10, 11, 12, 13, 14, 15, 16, 17, 18, 19 or 20 carbon atoms and at least one double bond. It is an embodiment of the application that, in the alkenyl groups, one or more, including all, of the hydrogen atoms are optionally replaced with F or $^2$H and thus include, for example trifluoroethenyl, pentafluoropropenyl and the like.

The term "alkynyl" as used herein, whether it is used alone or as part of another group, means straight or branched chain, unsaturated alkynyl groups. The term $C_{2-6}$alkenyl means an alkenyl group having 2, 3, 4, 5, or 6 carbon atoms and at least one triple bond. The term $C_{2-20}$alkenyl means an alkenyl group having 2, 3, 4, 5, 6, 7, 8, 9, 10, 11, 12, 13, 14, 15, 16, 17, 18, 19 or 20 carbon atoms and at least one triple bond. It is an embodiment of the application that, in the alkynyl groups, one or more, including all, of the hydrogen atoms are optionally replaced with F or $^2$H.

The term "cycloalkyl" as used herein, whether it is used alone or as part of another group, means cyclic, saturated alkyl groups. The term $C_{3-10}$cycloalkyl means a cycloalkyl group having 3, 4, 5, 6, 7, 8, 9 or 10 carbon atoms. It is an embodiment of the application that, in the cycloalkyl groups, one or more, including all, of the hydrogen atoms are optionally replaced with F or $^2$H.

The term "cycloalkenyl" as used herein, whether it is used alone or as part of another group, means cyclic, unsaturated alkyl groups. The term $C_{3-10}$cycloalkenyl means a cycloalkenyl group having 3, 4, 5, 6, 7, 8, 9 or 10 carbon atoms and at least one double bond. It is an embodiment of the application that, in the cycloalkenyl groups, one or more, including all, of the hydrogen atoms are optionally replaced with F or $^2$H.

The term "heterocycloalkyl" as used herein, whether it is used alone or as part of another group, means cyclic, saturated alkyl groups containing at least one heteroatom, such as N, O, and/or S. The term $C_{3-10}$cycloalkyl means a cycloalkyl group having 3, 4, 5, 6, 7, 8, 9 or 10 carbon atoms, in which at least one of the carbon atoms has been replaced with a heteroatom, such as N, O and/or S. It is an embodiment of the application that, in the heterocycloalkyl groups, one or more, including all, of the hydrogen atoms are optionally replaced with F or $^2$H.

The term "aryl" as used herein refers to cyclic groups that contain at least one aromatic ring. In an embodiment of the application, the aryl group contains 6, 9 or 10 atoms, such as phenyl, naphthyl or indanyl. It is an embodiment of the application that, in the aryl groups, one or more, including all, of the hydrogen atoms are optionally replaced with F or $^2$H and thus include, for example pentafluorophenyl and the like.

The term "heteroaryl" as used herein refers to cyclic groups that contain at least one aromatic ring and at least one heteroatom, such as N, O and/or S. The term $C_{5-10}$heteroaryl means an aryl group having 5, 6, 7, 8, 9 or 10 atoms, in which at least one atom is a heteroatom, such as N, O and/or S. It is an embodiment of the application that, in the heteroaryl groups, one or more, including all, of the hydrogen atoms are optionally replaced with F or $^2$H and thus include, for example pentafluorophenyl and the like.

The term "sp$^2$ hybridized" as used herein refers to carbon atoms that are bonded to other atoms by one double bond and two single bonds.

The term "sp$^3$ hybridized" as used herein refers to carbon atoms where all bonds to other atoms are single bonds.

The term "reducing agent" as used herein means any compound or combination of compounds that reduces a desired functional group. A reducing agent results in the overall addition of electrons, including electrochemical addition of electrons, or in the case of organic chemistry, hydrogen atoms to the functional group.

The term "functionalization agent" as used herein refers to any compound or combination of compounds that reacts with an N-demethylated heterocyclic compound of the invention to result in the addition of an "R$^2$" group to the N atom, wherein R$^2$ is as defined herein. In a specific embodiment, the functionalization agent is a compound of Formula III or IV as defined herein.

As used herein, the term "acylation" and the related term "acylating agent" are used in the broadest sense to encompass any reaction in which an acyl group (a group comprising "C(O)—") is added to a compound. This includes reactions in which the acyl group is derived from carboxylic acid. It also includes, for example, the addition of an acetyl group. Types of acylating agents that may be used in the present invention include, but are not limited to, anhydrides, dicarbonates, dicarbamic agents and other known acylating agents.

The term "oxidant" as used herein refers to a reagent that provides an oxygen species for participation in the metal catalyzed reactions of the present application. In an embodiment, the oxygen source is O$_2$ gas, air or an inorganic or organic peroxide (i.e. a compound comprising an "O—O" functionality).

t-Boc as used herein refers to the group t-butyloxycarbonyl.

Ac as used herein refers to the group acetyl.

Ts (tosyl) as used herein refers to the group p-toluenesulfonyl

Ms as used herein refers to the group methanesulfonyl

TBDMS as used herein refers to the group t-butyldimethylsilyl.

TBDPS as used herein refers to the group t-butyldiphenylsilyl.

TMS as used herein refers to the group trimethylsilyl.

Tf as used herein refers to the group trifluoromethanesulfonyl.

Ns as used herein refers to the group naphthalene sulphonyl.

Bn as used herein refers to the group benzyl.

Fmoc as used herein refers to the group fluorenylmethoxycarbonyl.

Me as used herein refers to the group methyl.

Et as used herein refers to the group ethyl.

Ph as used herein refers to the group phenyl.

Bn as used herein refers to the group benzyl.

Pr as used herein refers to the group propyl.

Bu as used herein refers to the group butyl.

The term "leaving group" or "LG" as used herein refers to a group that is readily displaceable by a nucleophile, for example, under nucleophilic substitution reaction conditions. Examples of suitable leaving groups include, but are not limited to, halo, OMs, OTs, ONs, OTf, $C_{1-6}$acyl, and the like.

The terms "protective group" or "protecting group" or "PG" or the like as used herein refer to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, 3$^{rd}$ Edition, 1999 and in Kocienski, P. Protecting Groups, 3rd Edition, 2003, Georg Thieme Verlag (The Americas). Examples of suitable protecting groups include, but are not limited to t-Boc, Ac, Ts, Ms, silyl ethers such as TMS, TBDMS, TBDPS, Tf, Ns, Bn, Fmoc, benzoyl, dimethoxytrityl, methoxyethoxymethyl ether, methoxymethyl ether, pivaloyl, p-methoxybenzyl ether, tetrahydropyranyl, trityl, ethoxyethyl ethers, carbobenzyloxy, benzoyl and the like.

The expression "proceed to a sufficient extent" as used herein with reference to the reactions or process steps disclosed herein means that the reactions or process steps proceed to an extent that conversion of the starting material or substrate to product is maximized. Conversion may be maximized when greater than about 5, 10, 15, 20, 25, 30, 35, 40, 50, 55, 60, 65, 70, 75, 80, 85, 90, 95 or 100% of the starting material or substrate is converted to product.

II. Methods of the Invention

The present invention provides a one pot method for the N-demethylation and N-functionalization of a tertiary N-methylated heterocycle comprising reacting a N-methylated heterocycle substrate with a functionalization agent in the presence of a catalyst.

In one embodiment, the present invention provides a one pot method for the N-demethylation and N-functionalization of a tertiary N-methylated heterocycle comprising reacting a N-methylated heterocycle substrate with a functionalization agent, other than a haloformate ester, in the presence of a catalyst to obtain an N-functionalized heterocyclic derivative product. The method of the present application advantageously provides the N-functionalized product at lower temperatures than methods reported in the literature.

Some of the N-functionalized heterocyclic derivative products produced using the method of the invention are morphine alkaloid derivatives, the identity of which will, of course, vary with the tertiary N-methylated heterocycle substrate. Accordingly, the present application includes a method of preparing a compound of Formula I:

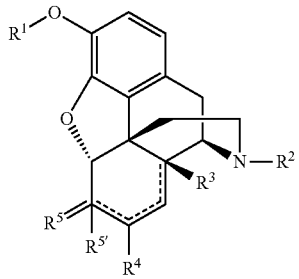
(I)

comprising reacting a compound of Formula II:

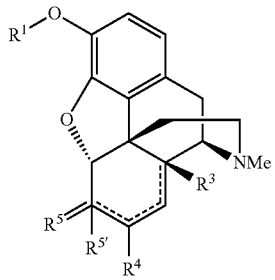
(II)

in the presence of a transition metal catalyst and a compound of Formula III or IV:

$$R^2\text{-LG} \quad (III)$$

$$R^6{=}C{=}O \quad (IV)$$

wherein, $R^1$ is selected from H, $C_{1-10}$alkyl, $C(O)C_{1-10}$alkyl, $C(O)OC_{1-10}$alkyl and $PG^1$;

$R^2$ is selected from $C(O)R^6$, $C(O)OR^6$, $S(O)R^6$, $SO_2R^6$, $P(O)R^6R^{6'}$, $P(O)(OR^6)R^{6'}$, $P(O)(OR^6)(OR^{6'})$, $C(O)NR^6R^{6'}$ and $C(O)SR^6$;

$R^3$ is selected from H, OH, $OC_{1-10}$alkyl, $OC(O)C_{1-10}$alkyl, $OC(O)OC_{1-10}$alkyl and $OPG^2$ or $R^3$ is not present when the carbon atom to which it is attached is $sp^2$ hybridized, or $R^3$ and $R^{5'}$ form a $CH_2$—$CH_2$ linker between the carbon atoms to which they are attached;

$R^4$ is selected from H, $C_{1-10}$alkyl, $C(O)C_{1-10}$alkyl, hydroxyl-substituted $C_{1-10}$alkyl, and $PG^3$-O-substituted $C_{1-10}$alkyl;

$R^5$ is selected from OH, $OC_{1-10}$alkyl, $OC(O)C_{1-10}$alkyl, $OC(O)OC_{1-10}$alkyl and $OPG^4$ when the ═ to which it is attached is a single bond, or $R^5$ is O when the ═ to which it is attached is a double bond, $R^{5'}$ is either not present or $R^{5'}$ and $R^3$ form a $CH_2$—$CH_2$ linker between the carbon atoms to which they are attached, only when $R^5$ ═ is $R^5$— and the carbon to which it is attached is $sp^3$ hybridized;

$R^6$ and $R^{6'}$ are independently selected from $C_{3-10}$cycloalkyl, $C_{3-10}$heterocycloalkyl, $C_{3-10}$cycloalkenyl, $C_{1-20}$alkyl, $C_{2-20}$alkenyl, $C_{2-20}$alkynyl, $C_{6-10}$aryl and $C_{5-10}$heteroaryl, each of the latter eight groups being unsubstituted or substituted with one or more substituents independently selected from $R^7$, $OR^8$, $SiR^7R^{7'}R^8$, $NR^8R^{8'}$, $SR^8$, $S(O)R^7$, $SO_2R^7$, halo, CN and $NO_2$;

$R^7$ and $R^{7'}$ are independently selected from $C_{1-6}$alkyl, $C_{6-10}$aryl and $C_{1-6}$alkylene$C_{6-10}$aryl;

$R^8$ and $R^{8'}$ are independently selected from H, $PG^5$, $C_{1-6}$alkyl, $C_{6-10}$aryl and $C_{1-6}$alkylene$C_{6-10}$aryl;

═ represents a single or double bond, provided that two double bonds are not adjacent to each other;

$PG^1$, $PG^2$, $PG^3$, $PG^4$ and $PG^5$ are independently, a protecting group that is removable after the preparation of the compound of Formula I; and LG is a leaving group, wherein, when (a) $R^1$, $R^8$ and/or $R^{8'}$ are H; (b) $R^3$ and/or $R^5$ is OH; and/or (c) $R^4$ is hydroxyl-substituted $C_{1-10}$alkyl, the method further comprises removal of any $R^2$ group in $R^1$, $R^8$, $R^{8'}$, $R^3$, $R^5$ and/or $R^4$.

In an embodiment of the invention, the method of preparing the compound of Formula I further comprises reacting the compound of Formula II with a compound of Formula III or IV, in the presence of a transition metal catalyst and an oxidant.

In an embodiment of the invention $R^1$ is selected from H, $C_{1-6}$alkyl, $C(O)C_{1-6}$alkyl, $C(O)OC_{1-6}$alkyl and $PG^1$. In a further embodiment, $R^1$ is selected from H, Me, Et, C(O)Me, C(O)Et, C(O)OMe, C(O)OEt and $PG^1$.

In an embodiment of the invention, $R^2$ is selected from $C(O)R^6$, $C(O)OR^6$, and $C(O)NR^6R^{6'}$. In another embodiment $R^2$ is $C(O)R^6$.

In an embodiment of the invention, $R^3$ is selected from H, OH, $OC_{1-6}$alkyl, $OC(O)C_{1-6}$alkyl, $OC(O)OC_{1-6}$alkyl and $OPG^2$ or $R^3$ is not present when the carbon atom to which it is attached is $sp^2$ hybridized. In another embodiment, $R^3$ is selected from H, OH, OMe, OEt, OC(O)Me, OC(O)Et, OC(O)OMe, OC(O)OEt and $OPG^2$ or $R^3$ is not present when the carbon atom to which it is attached is $sp^2$ hybridized. In yet another embodiment $R^3$ is selected from H, OH, OC(O)Me and $OPG^2$ or $R^3$ is not present when the carbon atom to which it is attached is $sp^2$ hybridized.

In an embodiment of the invention, $R^4$ is selected from H, $C(O)C_{1-6}$alkyl, hydroxyl-substituted $C_{1-10}$alkyl and $PG^3$-O-substituted $C_{1-10}$alkyl. In another embodiment, $R^4$ is selected from H, $C(O)C_{1-4}$alkyl and hydroxyl-substituted $C_{2-8}$alkyl. In yet another embodiment, $R^4$ is selected from H, C(O)Me and C(Me)(OH)(t-butyl).

In an embodiment of the invention, the ═ to which $R^5$ is attached is a single bond and $R^5$ is selected from OH, $OC_{1-6}$alkyl, $OC(O)C_{1-6}$alkyl, $OC(O)OC_{1-6}$alkyl and $OPG^4$. In a further embodiment, the ═ to which $R^5$ is attached is a single bond and $R^5$ is selected from OH, OMe, OEt, OC(O)Me, OC(O)Et, OC(O)OMe, OC(O)OEt and $OPG^4$. In yet another embodiment, the ═ to which $R^5$ is attached is a single bond and $R^5$ is selected from OH, OMe, OC(O)Me and $OPG^4$. In yet another embodiment of the invention, the ═ to which $R^5$ is attached is a double bond and $R^5$ is O.

In an embodiment of the invention $R^3$ and $R^{5'}$ form a $CH_2$—$CH_2$ linker between the carbon atoms to which they are attached.

In an embodiment of the invention, $R^6$ and $R^{6'}$ are independently selected from $C_{3-7}$cycloalkyl, $C_{3-7}$heterocycloalkyl, $C_{3-7}$cycloalkenyl, $C_{1-15}$alkyl, $C_{2-15}$alkenyl, $C_{2-15}$alkynyl, $C_{6-10}$aryl and $C_{6-10}$heteroaryl, each of the latter eight groups being unsubstituted or substituted with one, two, three or four substituents independently selected from $R^7$, $OR^8$, halo, CN and $NO_2$. In another embodiment, $R^6$ and $R^{6'}$ are independently selected from cyclopropyl, cyclobutyl, cyclopentyl, cyclohexyl, Me, Et, i-Pr, Pr, n-Bu, s-Bu, t-Bu, n-pentyl, n-hexyl, n-heptyl, n-octyl, n-nonyl, n-decyl, n-undecyl, allyl, propargyl, and phenyl, each of these groups being unsubstituted.

In an embodiment of the invention, $R^7$ and $R^{7'}$ are independently selected from Me, Et, Ph and Bn.

In an embodiment of the invention, $R^8$ and $R^{8'}$ are independently selected from H, $PG^5$, Me, Et, Ph and Bn.

In an embodiment of the application, $PG^1$, $PG^2$, $PG^3$, $PG^4$ and $PG^5$ are independently, any suitable protecting group that is removable after the preparation of the compound of Formula I. The selection of a suitable protecting group will depend on the identity of other functional groups present in the compounds, and the reaction conditions, but is within the skill of a person in the art. For example, suitable protecting groups include, but are not limited to, t-Boc, Ac, Ts, Ms, silyl ethers such as TMS, TBDMS and TBDPS, Tf, Ns, Bn, Fmoc, benzoyl, dimethoxytrityl, methoxyethoxymethyl ether, methoxymethyl ether, pivaloyl, p-methyoxybenzyl ether, tetrahydropyranyl, trityl, ethoxyethyl ethers, carbobenzyloxy, benzoyl and the like.

In an embodiment of the application, LG is any suitable leaving group. In a further embodiment, LG also electrophilically activates the adjacent group for reaction with a nucleophile. In a further embodiment, LG is Cl, Br, CN, $CCl_3$, imidazole, pentafluorophenyl, acyl, O—$R^2$, S—$R^2$, NH—$R^2$, OTs, ONs, OMs, or any activating group, for example activating groups used in peptide synthesis. In a specific embodiment, LG is Cl or O—$R^2$.

As noted above, ═ represents a single or double bond, provided that two double bonds are not adjacent to each other. In an embodiment, the ═ bonds, $R^3$, $R^4$ and $R^5$ are selected to provide a compound of Formula II(a):

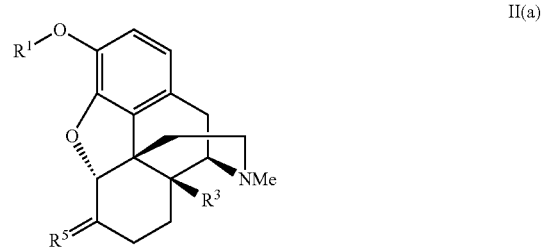

II(a)

wherein $R^1$ is H, $C_{1-10}$alkyl, $C(O)C_{1-10}$alkyl, $C(O)OC_{1-10}$alkyl or $PG^1$ (suitably H, Me, $PG^1$ or C(O)Me); $R^3$ is H, OH, $OC_{1-10}$alkyl, $OC(O)C_{1-10}$alkyl, $OC(O)OC_{1-10}$alkyl or $OPG^2$ (suitably H, OC(O)Me, $OPG^2$ or OH); and $R^5$ is OH, $OC_{1-10}$alkyl, $OC(O)C_{1-10}$alkyl, $OC(O)OC_{1-10}$alkyl or $OPG^4$, (suitably OH, OC(O)Me, $OPG^4$ or OMe), when ═ is a single bond and $R^5$ is O when ═ is a double bond;

or a compound of Formula II(b)

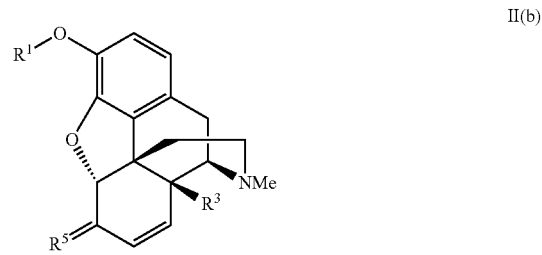

II(b)

wherein $R^1$ is H, $C_{1-10}$alkyl, $C(O)C_{1-10}$alkyl, $C(O)OC_{1-10}$alkyl or $PG^1$ (suitably H, Me, $PG^1$ or C(O)Me); $R^3$ is H, OH, $OC_{1-10}$alkyl, $OC(O)C_{1-10}$alkyl, $OC(O)OC_{1-10}$alkyl or $OPG^2$ (suitably H, OC(O)Me, $OPG^2$ or OH); and $R^5$ is OH, $OC_{1-10}$alkyl, $OC(O)C_{1-10}$alkyl, $OC(O)OC_{1-10}$alkyl or $OPG^4$ (suitably OH, $OPG^4$, OC(O)Me or OMe), when ═ is a single bond and $R^5$ is O when ═ is a double bond;

or a compound of Formula II(c):

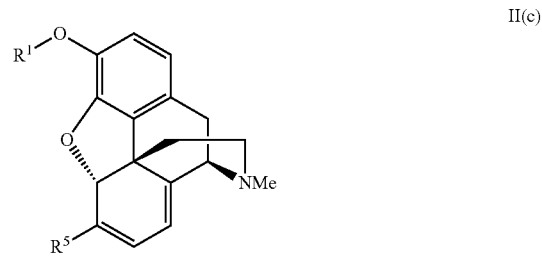

II(c)

wherein $R^1$ is H, $C_{1-10}$alkyl, $C(O)C_{1-10}$alkyl, $C(O)OC_{1-10}$alkyl or $PG^1$ (suitably H, Me, $PG^1$ or C(O)Me); and $R^5$ is OH, $OC_{1-10}$alkyl, $OC(O)C_{1-10}$alkyl, $OC(O)OC_{1-10}$alkyl or $OPG^4$, (suitably OH, $OPG^4$, OC(O)Me or OMe);

or a compound of Formula II(d):

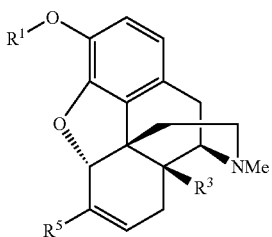

II(d)

wherein R$^1$ is H, C$_{1-10}$alkyl, C(O)C$_{1-10}$alkyl, C(O)OC$_{1-10}$alkyl or PG$^1$ (suitably H, Me, PG$^1$ or C(O)Me); R$^3$ is H, OH, OC$_{1-10}$alkyl, OC(O)C$_{1-10}$alkyl, OC(O)OC$_{1-10}$alkyl or OPG$^2$ (suitably H, OPG$^2$, OC(O)Me or OH); and R$^5$ is OH, OC$_{1-10}$alkyl, OC(O)C$_{1-10}$alkyl, OC(O)OC$_{1-10}$alkyl or OPG$^4$ (suitably OH, OPG$^4$, OC(O)Me or OMe);

or a compound of the Formula II(e):

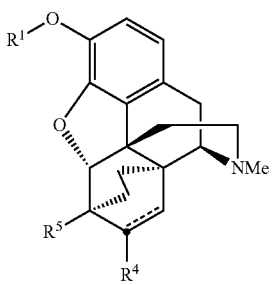

II(e)

wherein R$^1$ is H, C$_{1-10}$alkyl, C(O)C$_{1-10}$alkyl, C(O)OC$_{1-10}$alkyl or PG$^1$ (suitably H, Me, PG$^1$ or C(O)Me); R$^4$ is H, C$_{1-10}$alkyl, C(O)C$_{1-10}$alkyl, hydroxyl-substituted C$_{1-10}$alkyl or PG$^3$-O-substituted C$_{1-10}$alkyl (suitably C(Me)(OH)(t-butyl) or C(O)Me); R$^5$ is OH, OC$_{1-10}$alkyl, OC(O)C$_{1-10}$alkyl, OC(O)OC$_{1-10}$alkyl or OPG$^4$ (suitably OH, OPG$^4$, OC(O)Me or OMe); and ═ is a single or double bond (suitably a single bond).

Use of the compounds of Formula II(a), II(b), II(c), II(d) and II(e) provide the corresponding compounds of Formula I(a), I(b), I(c), I(d) and I(e), respectively:

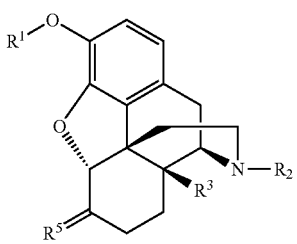

I(a)

wherein R$^1$ is H, C$_{1-10}$alkyl, C(O)C$_{1-10}$alkyl, C(O)OC$_{1-10}$alkyl or PG$^1$ (suitably H, Me, PG$^1$ or C(O)Me); R$^2$ is as defined in Formula I; R$^3$ is H, OH, OC$_{1-10}$alkyl, OC(O)C$_{1-10}$alkyl, OC(O)OC$_{1-10}$alkyl or OPG$^2$ (suitably H, OPG$^2$, OC(O)Me or OH); and R$^5$ is OH, OC$_{1-10}$alkyl, OC(O)C$_{1-10}$alkyl, OC(O)OC$_{1-10}$alkyl or OPG$^4$, (suitably OH, OPG$^4$, OC(O)Me or OMe), when ═ is a single bond and R$^5$ is O when ═ is a double bond;

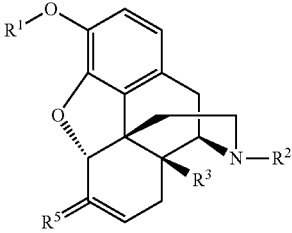

I(b)

wherein R$^1$ is H, C$_{1-10}$alkyl, C(O)C$_{1-10}$alkyl, C(O)OC$_{1-10}$alkyl or PG$^1$ (suitably H, Me, PG$^1$ or C(O)Me); R$^2$ is as defined in Formula I; R$^3$ is H, OH, OC$_{1-10}$alkyl, OC(O)C$_{1-10}$alkyl, OC(O)OC$_{1-10}$alkyl or OPG$^2$ (suitably H, OPG$^2$, OC(O)Me or OH); and R$^5$ is OH, OC$_{1-10}$alkyl, OC(O)C$_{1-10}$alkyl, OC(O)OC$_{1-10}$alkyl or OPG$^4$ (suitably OH, OPG$^4$, OC(O)Me or OMe), when ═ is a single bond and R$^5$ is O when ═ is a double bond;

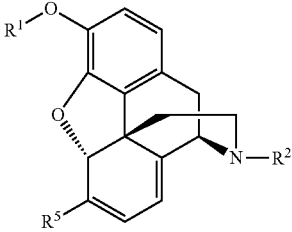

I(c)

wherein R$^1$ is H, C$_{1-10}$alkyl, C(O)C$_{1-10}$alkyl, C(O)OC$_{1-10}$alkyl or PG$^1$ (suitably H, Me, PG$^1$ or C(O)Me); R$^2$ is as defined in Formula I; and R$^5$ is OH, OC$_{1-10}$alkyl, OC(O)C$_{1-10}$alkyl, OC(O)OC$_{1-10}$alkyl or OPG$^4$, (suitably OH, OPG$^4$, OC(O)Me or OMe);

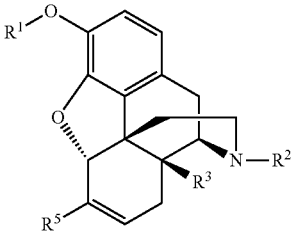

I(d)

wherein R$^1$ is H, C$_{1-10}$alkyl, C(O)C$_{1-10}$alkyl, C(O)OC$_{1-10}$alkyl or PG$^1$ (suitably H, Me, PG$^1$ or C(O)Me); R$^2$ is as defined in Formula I; R$^3$ is H, OH, OC$_{1-10}$alkyl, OC(O)C$_{1-10}$alkyl, OC(O)OC$_{1-10}$alkyl or OPG$^2$ (suitably H, OPG$^2$, OC(O)Me or OH); and R$^5$ is OH, OC$_{1-10}$alkyl, OC(O)C$_{1-10}$alkyl, OC(O)OC$_{1-10}$alkyl or OPG$^4$ (suitably OH, OPG$^4$, OC(O)Me or OMe);

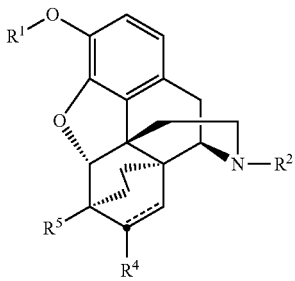

I(e)

wherein R¹ is H, $C_{1-10}$alkyl, $C(O)C_{1-10}$alkyl, $C(O)OC_{1-10}$alkyl or PG¹ (suitably H, Me, PG¹ or C(O)Me); R² is as defined in Formula I; R⁴ is H, $C_{1-10}$alkyl, $C(O)C_{1-10}$alkyl, hydroxyl-substituted $C_{1-10}$alkyl or PG³-O-substituted $C_{1-10}$alkyl (suitably C(Me)(OH)(t-butyl) or C(O)Me); R⁵ is OH, $OC_{1-10}$alkyl, $OC(O)C_{1-10}$alkyl, $OC(O)OC_{1-10}$alkyl or OPG⁴ (suitably OH, OPG⁴, OC(O)Me or OMe); and ⁼ is a single or double bond (suitably a single bond).

Specific examples of morphine derivatives that may be produced using the present methodology include, but are not limited to, N-functionalized derivatives of thebaine, oripavine, 14-hydroxycodeinone, 14-hydroxymorphinone, morphine, codeine, hydromorphone, hydrocodone, oxymorphone, oxycodone, hydromorphol, oxymorphol and [5α,7α]-(1,1-dimethylethyl)-4,5-epoxy-18,19-dihydro-3,6-dimethoxy-α,17-dimethyl-6,14-ethenomorphinan-7-methanol, which are intermediates for use in the manufacture of pharmaceuticals such as, but not limited to, naloxone, naltrexone, nalbuphone and buprenophine.

In an embodiment, R¹ is PG¹, R³ (when present) is OPG² and/or R⁵ (when present) is OPG⁴ and the invention further includes reacting the compounds of Formula I under conditions to remove PG¹, PG² and/or PG⁴ to provide the corresponding free hydroxyl groups. A person skilled in the art would know the conditions to use based on the identity of the PGs.

In an alternate embodiment, the present invention provides a one pot method for the N-demethylation and N-acylation of tertiary N-methylated morphine alkaloids comprising reacting a N-methylated morphine alkaloid substrate with an acylating agent selected from the group consisting of anhydrides and dicarbonates in the presence of a catalyst to obtain an N-acylated morphine alkaloid derivative product.

In particular the invention provides a method for catalysed N-demethylation and N-acylation wherein the N-methylated heterocycle is a morphine alkaloid or a derivative thereof or a tropane alkaloid or derivative thereof.

In another embodiment of the invention, the N-methylated compound is a tropane alkaloid. Accordingly, the present invention includes a method of preparing an N—R²-functionalized tropane alkaloid comprising reacting an N-methyl tropane alkaloid in the presence of a transition metal catalyst and a compound of Formula III or IV:

R²-LG (III)

R⁶=C=O (IV)

wherein,

R² is selected from C(O)R⁶, C(O)OR⁶, S(O)R⁶, SO₂R⁶, P(O)R⁶R⁶', P(O)(OR⁶)R⁶', P(O)(OR⁶)(OR⁶'), C(O)NR⁶R⁶' and C(O)SR⁶;

R⁶ and R⁶' are independently selected from $C_{3-10}$cycloalkyl, $C_{3-10}$heterocycloalkyl, $C_{3-10}$cycloalkenyl, $C_{1-20}$alkyl, $C_{2-20}$alkenyl, $C_{2-20}$alkynyl, $C_{6-10}$aryl and $C_{5-10}$heteroaryl, each of the latter eight groups being unsubstituted or substituted with one or more substituents independently selected from R⁷, OR⁸, SiR⁷R⁷'R⁸, NR⁸R⁸', SR⁸, S(O)R⁷, SO₂R⁷, halo, CN and NO₂;

R⁷ and R⁷' are independently selected from $C_{1-6}$alkyl, $C_{6-10}$aryl and $C_{1-6}$alkylene$C_{6-10}$aryl;

R⁸ and R⁸' are independently selected from H, PG⁵, $C_{1-6}$alkyl, $C_{6-10}$aryl and $C_{1-6}$alkylene$C_{6-10}$aryl;

PG⁵ is a protecting group that is removable after the preparation of the N—R²-functionalized tropane alkaloid; and LG is a leaving group, wherein, when R⁸ and/or R⁸' are H; the method further comprises removal of any R² group in R⁸ and/or R⁸'.

In an embodiment of the invention, the method of preparing a N—R²-functionalized tropane alkaloid further comprises reacting an N-methyl tropane alkaloid with a compound of Formula III or IV, in the presence of a transition metal catalyst and an oxidant.

Tropane derivatives are preferably selected from the group consisting of tropinone, tropane, tropine, atropine, cocaine, or any other bicyclo-[3.2.1]-azabicyclic methylamines.

In an embodiment, the conditions to remove R² groups are selected from deacylation conditions (for example, acid or basic hydrolysis or Schwartz' reagent (Cp₂ZrHCl)), desulfurization conditions and dephosphorylation conditions.

Examples of a demethylation/acylation reaction described herein, are shown below in which hydrocodone, protected oxomorphone and an intermediate in the preparation of buprenorphine are the N-methylated heterocycles. It will be understood that these examples merely illustrates three embodiments of the method of the invention described herein:

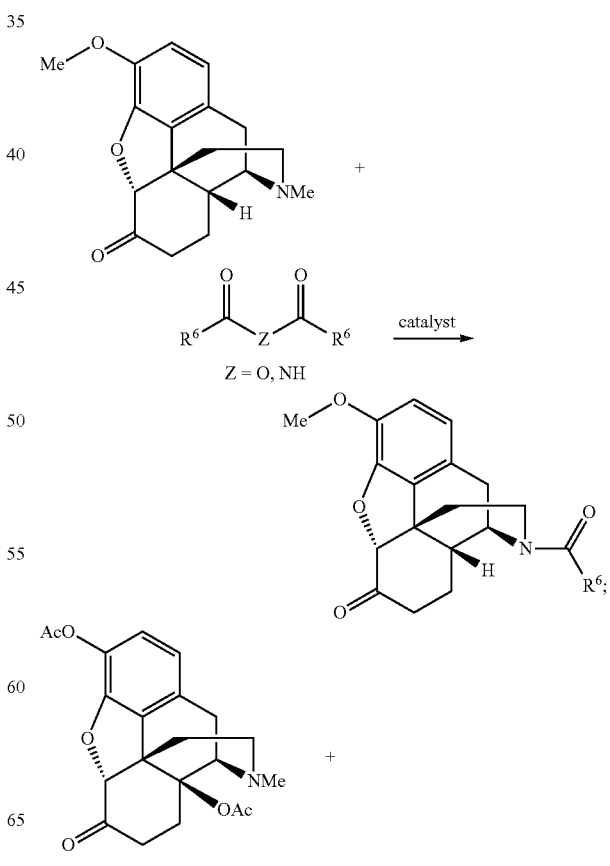

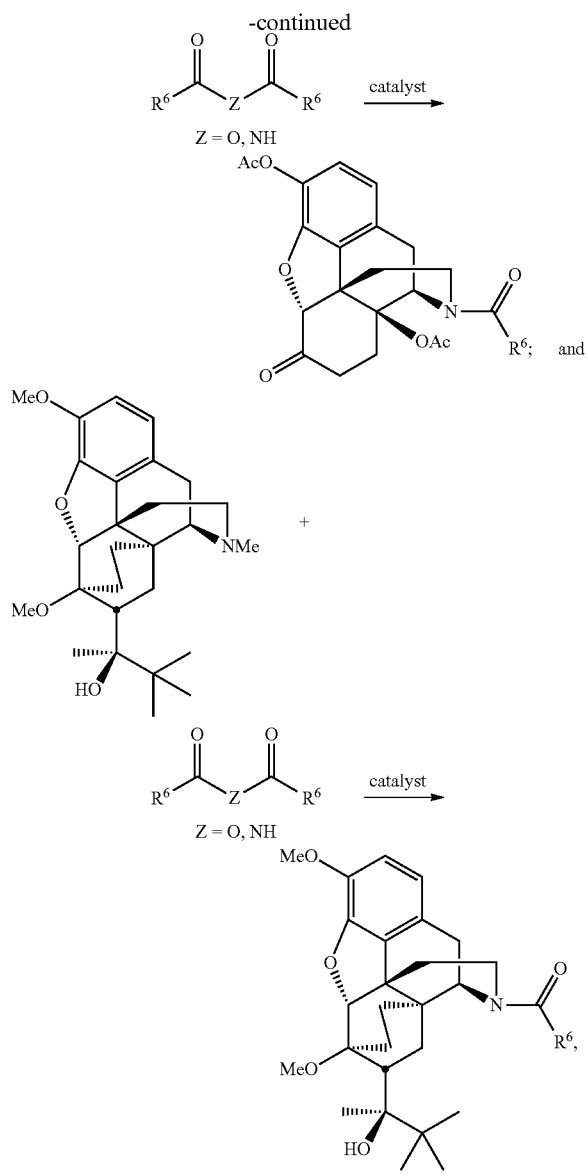

wherein $R^6$ is selected from $C_{3-10}$cycloalkyl, $C_{3-10}$heterocycloalkyl, $C_{3-10}$cycloalkenyl, $C_{1-20}$alkyl, $C_{2-20}$alkenyl, $C_{2-20}$alkynyl, $C_{6-10}$aryl and $C_{5-10}$heteroaryl, each of the latter eight groups being unsubstituted or substituted with one or more substituents independently selected from $R^7$, $OR^8$, $SiR^7R^{7'}R^8$, $NR^8R^{8'}$, $SR^8$, $S(O)R^7$, $SO_2R^7$, halo, CN and $NO_2$;

$R^7$ and $R^{7'}$ are independently selected from $C_{1-6}$alkyl, $C_{6-10}$aryl and $C_{1-6}$alkylene$C_{6-10}$aryl; and $R^8$ and $R^{8'}$ are independently selected from H, $PG^5$, $C_{1-6}$alkyl, $C_{6-10}$aryl and $C_{1-6}$alkylene$C_{6-10}$aryl. In an embodiment, $R^6$ is selected from cyclopropyl, cyclobutyl, cyclopentyl, cyclohexyl, Me, Et, i-Pr, Pr, n-Bu, s-Bu, t-Bu, n-pentyl, n-hexyl, n-heptyl, n-octyl, n-nonyl, n-decyl, n-undecyl, allyl and phenyl, each of the these groups being unsubstituted.

In an embodiment of the methods of the invention, the functionalization agent is an acylating agent. Various types of acylating agents can be used. The product that is obtained by the reaction can be customized through the selection of the starting material and the acylating agent.

In one embodiment, the acylating agent is a compound of Formula III(a):

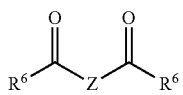

III(a)

wherein
Z is NH, S or O;
$R^6$ is selected from $C_{3-10}$cycloalkyl, $C_{3-10}$heterocycloalkyl, $C_{3-10}$cycloalkenyl, $C_{1-20}$alkyl, $C_{2-20}$alkenyl, $C_{2-20}$alkynyl, $C_{6-10}$aryl and $C_{5-10}$heteroaryl, each of the latter eight groups being unsubstituted or substituted with one or more substituents independently selected from $R^7$, $OR^8$, $SiR^7R^{7'}R^8$, $NR^8R^{8'}$, $SR^8$, $S(O)R^7$, $SO_2R_7$, halo, CN and $NO_2$;

$R^7$ and $R^{7'}$ are independently selected from $C_{1-6}$alkyl, $C_{6-10}$aryl and $C_{1-6}$alkylene$C_{6-10}$aryl; and $R^8$ and $R^{8'}$ are independently selected from H, $PG^5$, $C_{1-6}$alkyl, $C_{6-10}$aryl and $C_{1-6}$alkylene$C_{6-10}$aryl. In an embodiment, Z is O and $R^6$ is selected from cyclopropyl, cyclobutyl, cyclopentyl, cyclohexyl, Me, Et, i-Pr, Pr, n-Bu, s-Bu, t-Bu, n-pentyl, n-hexyl, n-heptyl, n-octyl, n-nonyl, n-decyl, n-undecyl, allyl, propargyl and phenyl, each of the these groups being unsubstituted.

One type of acylating agent that has been shown to be useful in the present invention is an anhydride. Preferred anhydrides for use in the invention include, but are not limited to, acetic anhydride, iso-butyric anhydride, n-propanoic anhydride, decanoic anhydride, dodecanoic anhydride, cyclopropylcarbonyl anhydride, cyclobutylcarbonyl anhydride, allyl carbonyl anhydride, anhydrides derived from $C_1$-$C_{19}$carboxylic acids and mixed anhydrides derived therefrom.

In another embodiment, the acylating agent is a dicarbonate of Formula III(b)

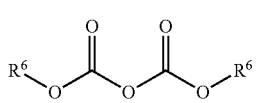

III(b)

wherein
$R^6$ is selected from $C_{3-10}$cycloalkyl, $C_{3-10}$heterocycloalkyl, $C_{3-10}$cycloalkenyl, $C_{1-20}$alkyl, $C_{2-20}$alkenyl, $C_{2-20}$alkynyl, $C_{6-10}$aryl and $C_{5-10}$heteroaryl, each of the latter eight groups being unsubstituted or substituted with one or more substituents independently selected from $R^7$, $OR^8$, $SiR^7R^{7'}R^8$, $NR^8R^{8'}$, $SR^8$, $S(O)R^7$, $SO_2R_7$, halo, CN and $NO_2$;

$R^7$ and $R^{7'}$ are independently selected from $C_{1-6}$alkyl, $C_{6-10}$aryl and $C_{1-6}$alkylene$C_{6-10}$aryl; and $R^8$ and $R^{8'}$ are independently selected from H, $PG^5$, $C_{1-6}$alkyl, $C_{6-10}$aryl and $C_{1-6}$alkylene$C_{6-10}$aryl. In an embodiment, Z is O and $R^6$ is selected from cyclopropyl, cyclobutyl, cyclopentyl, cyclohexyl, Me, Et, i-Pr, Pr, n-Bu, s-Bu, t-Bu, n-pentyl, n-hexyl, n-heptyl, n-octyl, n-nonyl, n-decyl, n-undecyl, allyl, propargyl and phenyl, each of the these groups being unsubstituted.

Examples of preferred dicarbonates include, but are not limited to, a mixed carbonate derivative of $C_1$-$C_{19}$ alcohols, dimethyl dicarbonate, di-tent-amyl dicarbonate, di-tert-butyl dicarbonate, diallyl pyrocarbonate, dibenzyl dicarbonate, diethyl pyrocarbonate, dimethyl dicarbonate, erythritol bis(carbonate) and mixed carbonates.

Alternatively, the acylating agent may be a dicarbamic anhydride of Formula III(c):

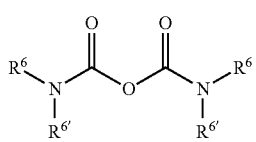

III(c)

$R^6$ and $R^{6'}$ are independently selected from $C_{3-10}$cycloalkyl, $C_{3-10}$heterocycloalkyl, $C_{3-10}$cycloalkenyl, $C_{1-20}$alkyl, $C_{2-20}$alkenyl, $C_{2-20}$alkynyl, $C_{6-10}$aryl and $C_{5-10}$heteroaryl, each of the latter eight groups being unsubstituted or substituted with one or more substituents independently selected from $R^7$, $OR^8$, $SiR^7R^{7'}R^8$, $NR^8R^{8'}$, $SR^8$, $S(O)R^7$, $SO_2R^7$, halo, CN and $NO_2$;

$R^7$ and $R^{7'}$ are independently selected from $C_{1-6}$alkyl, $C_{6-10}$aryl and $C_{1-6}$alkylene$C_{6-10}$aryl; and $R^8$ and $R^{8'}$ are independently selected from H, $PG^5$, $C_{1-6}$alkyl, $C_{6-10}$aryl and $C_{1-6}$alkylene$C_{6-10}$aryl. In an embodiment, $R^6$ and $R^{6'}$ are independently selected from cyclopropyl, cyclobutyl, cyclopentyl, cyclohexyl, Me, Et, i-Pr, Pr, n-Bu, s-Bu, t-Bu, n-pentyl, n-hexyl, n-heptyl, n-octyl, n-nonyl, n-decyl, n-undecyl, allyl, propargyl and phenyl, each of the these groups being unsubstituted.

Preferred dicarbamic anhydrides include, but are not limited to, N,N'-dimethylcarbamic anhydride, N,N' diethylcarbamic anhydride, diphenylcarbamic acid anhydride, N,N' diphenylcarbonic acid anhydride, N,N'-diphenyldicarbonic diamide, and mixtures thereof.

In a further alternative embodiment, the acylating agent is compound of Formula IV:

wherein $R^6$ is selected from $C_{3-10}$cycloalkyl, $C_{3-10}$heterocycloalkyl, $C_{3-10}$cycloalkenyl, $C_{1-20}$alkyl, $C_{2-20}$alkenyl, $C_{2-20}$alkynyl, $C_{6-10}$aryl and $C_{5-10}$heteroaryl, each of the latter eight groups being unsubstituted or substituted with one or more substituents independently selected from $R^7$, $OR^8$, $SiR^7R^{7'}R^8$, $NR^8R^{8'}$, $SR^8$, $S(O)R^7$, $SO_2R^7$, halo, CN and $NO_2$;

$R^7$ and $R^{7'}$ are independently selected from $C_{1-6}$alkyl, $C_{6-10}$aryl and $C_{1-6}$alkylene$C_{6-10}$aryl; and $R^8$ and $R^{8'}$ are independently selected from H, $PG^5$, $C_{1-6}$alkyl, $C_{6-10}$aryl and $C_{1-6}$alkylene$C_{6-10}$aryl. In an embodiment, $R^6$ is selected from cyclopropyl, cyclobutyl, cyclopentyl, cyclohexyl, Me, Et, i-Pr, Pr, n-Bu, s-Bu, t-Bu, n-pentyl, n-hexyl, n-heptyl, n-octyl, n-nonyl, n-decyl, n-undecyl, allyl, propargyl and phenyl, each of the these groups being unsubstituted.

The catalyst is any suitable transition metal catalyst, including elemental metals and salts thereof or any other derivative. In an embodiment, the catalyst is one wherein the active metal comprises W, V, Cu, Fe, Ru, Co, Rh, Ir, Ni, Pt, Ge, Sn, Os, Cu, Ag, Au, Pb and/or Pd. Examples of complexes/compounds which can be used as the catalyst include, but are not limited to, catalysts comprising palladium, platinum (e.g. $PtCl_2$ and $K_2PtCl_4$), ruthenium (e.g. Ru/C, $RuCl_3 \times H_2O$, $RuCl_2(PPh_3)_3$, $RuO_2$, and tetrapropylammonium perruthenates), iron (e.g. $FeCl_2$, $FeSO_4$, and iron carbonyls like $Fe_2(CO)_9$), tungsten (e.g. $Na_2WO_4$), vanadium (e.g. $VO(acac)_2$), iridium, copper (e.g. CuBr), gold, and silver complexes. In an embodiment, the catalyst is a Pd(0) or Pd(II) catalyst, for example, but not limited to $Pd(OAc)_2$, $PdCl_2$, $PdCl_2(PPh_3)_4$, $PdBr_2$, $Pd(acac)_2$, $Pd_2(dba)_3$, $Pd(dba)_2$, $Pd(PPh_3)_4$, Pd black or palladium-perovskites, or Pd(0) or Pd(II) catalysts on any type of solid support (e.g. charcoal, sulfates, carbonates, alumina) or in encapsulated form.

A preferred catalyst for use in the methods of the invention is a Pd catalyst, such as Pd, $PdCl_2$, $Pd(OAc)_2$, $Pd(acac)_2$, $Pd(PPh_3)_4$ and $Pd(dba)_2$. In a preferred embodiment the palladium catalyst is $Pd(OAc)_2$.

In one embodiment of the method a combination of catalysts may be employed, e.g. a catalyst such as a Pd catalyst with a co-catalyst. Examples of a co-catalyst include, but are not limited to, copper salts, such as $CuCl_2$, $Cu(OAc)_2$ and $Cu(acac)_2$, and all oxophilic metals and their complexes, such as cerium salts.

In another embodiment, the total amount of catalyst used in the methods of the invention is about 0.01 mol % to about 20 mol %, about 1 mol % to about 15 mol % or about 5 mol % to about 10 mol %.

In a further embodiment, the amount of catalytic palladium is preferably in the range of about 0.0001 equivalents to 1.2 equivalents. Preferably the amount of catalytic palladium is in the range of about 0.01 equivalents to 0.2 equivalents. More preferably the amount of catalytic palladium is about 0.1 equivalents.

In an embodiment, the method of the invention is suitably carried out in the presence of an oxidant, either through the use of added $O_2$ gas, electrochemical oxidation and/or oxidant, and/or by simply carrying out the reaction in an air atmosphere. Examples of suitable oxidants, include, but are not limited to organic and inorganic peroxides, such as t-butylhydroperoxide, cumenehydroperoxide, dibutylperoxide, laurylperoxide, hydrogenperoxide, perborates and $K_2S_2O_8$ and mixtures thereof.

The methods/reactions of the invention may optionally include the addition of a solvent, including polar solvents, aprotic polar solvents, aqueous solvents, non-polar organic solvents, including but not limited to, water, dimethylformamide (DMF), benzene, dioxane, toluene, acetonitrile and $C_1$-$C_4$ alcohols or a mixture of any of these. In a preferred embodiment the solvent is dioxane. The amount of solvent added is usually in the range of about 0.1-100 mL/gram of alkaloid.

The conversion of the compound of Formula II to the compound of Formula I is also suitably carried out in aqueous solutions or in an inert organic solvent or a mixture of solvents, such as, but not limited to, dioxane, toluene or benzene, DMF, acetonitrile, diethylcarbonate, ionic liquids, water, dilute aqueous acid and dilute aqueous base, and at temperatures and time sufficient for the conversion to proceed to a sufficient extent. Non-limiting examples of suitable temperatures are from about 10° C. to about 400° C., about 50° C. to about 200° C. or, about 75° C. to about 125° C. Examples of non-limiting reaction times are about 0.5 hours to about 64 hours, about 1 hour to about 48 hours, or about 5 hours to about 30 hours.

In one embodiment of the invention, hydrocodone, identified in Scheme 2 below, was treated with catalytic $Pd(OAc)_2$ in the presence of $Ac_2O$, and N-acetyl norhydrocodone was isolated. The X-ray crystal structure of this novel morphine analogue is represented in FIG. 1. In another embodiment, hydrocodone was treated with catalytic $Pd(OAc)_2$ in the presence of dimethyldicarbonate (see Scheme 2). This resulted in the production of N-methoxycarbonyl nor-hydrocodone.

Scheme 2

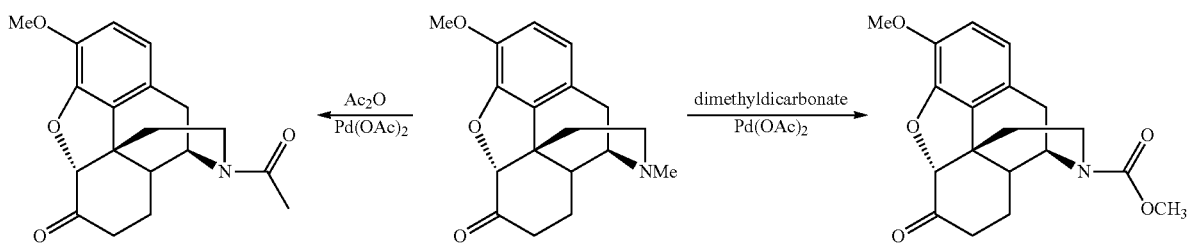

An interesting observation common to all conditions (described in greater detail in Examples 1a-j below) was the isolation of two isomers in a ratio of 3:1 in favour of the equatorial isomer.

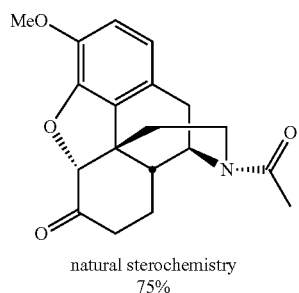

natural sterochemistry
75%

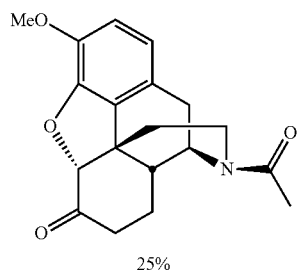

25%

In another embodiment of the invention, 14-acetyloxymorphone, identified in Scheme 3 below, was treated with catalytic Pd(OAc)$_2$ in the presence of Ac$_2$O in dioxane and N-acetyl-14-acetyloxymorphone was isolated as a mixture of axial and equatorial amide isomers (ratio 1:2).

Scheme 3

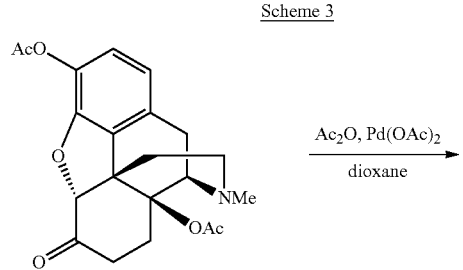

-continued

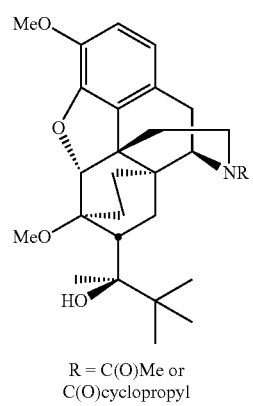

A series of reaction conditions were tested and it was found that Pd(OAc)$_2$ was a preferred catalyst and could be successfully used in the presence of air or O$_2$ and in the presence of absence of a co-catalyst and/or solvent. For the catalyst, Pd(acac)$_2$, it was optimal to perform the reaction in the presence of O$_2$.

In another embodiment of the invention, [5α,7α]-(1,1-dimethylethyl)-4,5-epoxy-18,19-dihydro-3,6-dimethoxy-α,17-dimethyl-6,14-ethenomorphinan-7-methanol, identified in Scheme 4 below, was treated with catalytic Pd(OAc)$_2$ in the presence of Ac$_2$O or cyclopropylcarboxylic acid anhydride, optionally, Cu(OAc)$_2$ and air or oxygen, in dioxane and the corresponding N-acyl compounds were isolated as a mixture of axial and equatorial amide isomers.

Scheme 4

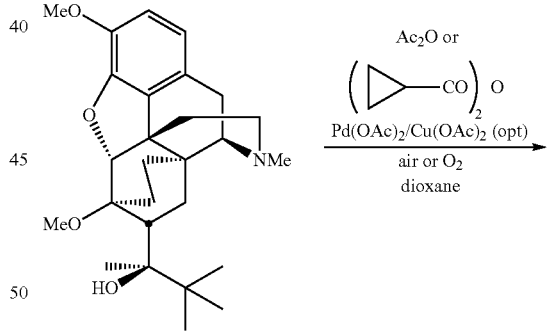

R = C(O)Me or C(O)cyclopropyl

Based on the success of the N-demethylation-acylation procedure, the reactivity of a series of anhydrides was explored. This resulted in the isolation of a novel range of N-acylated hydrocodone derivatives as described further in Example 2.

The utility of the method of the invention was further demonstrated using other N-methylated heterocycles including tropane and its derivatives. The compatibility of the method to a range of functional groups such as ketones and esters was also demonstrated as shown in Example 3 below.

The compounds of Formula I are useful intermediates in the preparation of morphine alkaloids. For example, when $R^2$ in the compounds of Formula I is an acyl group, this group may be treated to selectively reduce the carbonyl of the acyl group to provide the corresponding tertiary amine compound. Examples of such reducing agents include, but are not limited to, metal hydride reducing agents, hydrosilylation-based reducing agents, hydroalation-based reducing agents and hydroboration-based reducing agents. Examples of metal hydride reducing agents include, but are not limited to lithium aluminum hydride and sodium bis(2-methoxyethoxy)aluminum hydride. Hydrosilylation reagents typically comprise a silane and a catalyst based on complexes of platinum, rhodium, ruthenium, or other nobel metals and iron or zinc. Examples of silanes include, but are not limited to, poly(methylhydrosiloxane) (PMHS) and tetramethyldisiloxane (TMDS), and examples of catalysts include, but are not limited to, Karstedt's catalyst, Pt(COD)Cl$_2$, Ru$_3$(CO)$_{12}$, Fe$_2$(CO)$_9$ and Fe$_3$(CO)$_{12}$. Hydroalation reducing agents include, for example, AlH$_3$. In an embodiment, the reduction is carried out in the presence of excess PMHS or TMDS and 1-20 mol % of Karstedt's catalyst at a temperature of about 0° C. to about 100° C., in an inert organic solvent or mixture of solvents, such as toluene, for a time sufficient for the reduction to proceed to a sufficient extent, such as 5 min to about 48 hours, or about 1 hour to about 24 hours. In another embodiment, the reduction is carried out using lithium aluminum hydride or sodium bis(2-methoxyethoxy)aluminum hydride in an inert organic solvent or mixture of solvents at a temperature of about 0° C. to about 100° C., for a time sufficient for the reduction to proceed to a sufficient extent, such as 5 min to about 48 hours, or about 1 hour to about 24 hours. It is to be understood that, depending on the identity of the other R groups in the compound of Formula I, it is possible that the reducing conditions will reduce a functional group within one or more of these R groups. In fact it is an embodiment, that, when one or more protecting groups are present in the compound of Formula I, such as PG$^1$, PG$^2$, PG$^3$, PG$^4$ or PG$^5$, one or more of these protecting groups are also removed under the reducing conditions to avoid a deprotection step at the end of the preparation of a desired morphine alkaloid. Examples of protecting groups that are removable under reducing conditions include, but are not limited to alkyl carbonates. In an embodiment, an appropriate compound of Formula I is treated with a reducing agent to provide naltrexone, nalbuphone or buprenorphine.

In a further embodiment, when $R^2$ in the compounds of Formula I is an acyl group, this group may be selectively deacylated to the corresponding secondary amine. For example, deacylation conditions may comprise treating the compound of Formula I with an acid or a base at elevated temperatures. Examples of such conditions include, for example, alkylamines such as aminoalcohols or alkali hydroxides such as KOH, in glycol solvents, such as digol, at a temperature of about 100° C. to about 400° C., or about 100° C. to about 150° C., for a time sufficient for the reaction to proceed to a sufficient extent, such as about 1 hour to about 48 hours, or about 6 hours to about 18 hours. Under these conditions it is an embodiment that base-labile PGs are removed, such as C$_{1-6}$alkyl groups. In another embodiment, the deacylation conditions comprise Schwartz' reagent (Cp$_2$ZrHCl) in an inert organic solvent or mixture of solvents at a temperature of about 0° C. to about 100° C., or about 30° C. to about 80° C., for a time sufficient for the reaction to proceed to a sufficient extent, such as about 1 hour to about 48 hours, or about 6 hours to about 18 hours. In another embodiment, the deacylation conditions comprise aqueous acid conditions, such as aqueous HCl, at a temperature of about 50° C. to about 200° C., or about 80° C. to about 120° C., for a time sufficient for the reaction to proceed to a sufficient extent, such as about 1 hour to about 48 hours, or about 6 hours to about 18 hours. It is to be understood that, depending on the identity of the other R groups in the compound of Formula I, it is possible that the deacylation conditions will modify another functional group within one or more of these R groups. In fact it is an embodiment, that, when one or more protecting groups are present in the compound of Formula I, such as PG$^1$, PG$^2$, PG$^3$, PG$^4$ or PG$^5$, one or more of these protecting groups are also removed under the deacylation conditions to avoid a deprotection step at the end of the preparation of a desired morphine alkaloid.

Accordingly, the present invention also includes a method for the preparation of naltrexone or nalbuphone from a compound of Formula I(a):

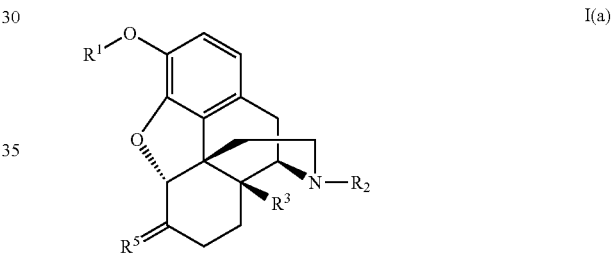

I(a)

wherein $R^1$ is H, $R^3$ is OH, ⚌ is a double bond, $R^5$ is O, $R^2$ is C(O)cyclopropyl or C(O)cyclobutyl, and the compound of Formula I(a) is prepared using the method of the invention, comprising:

(a) treating the compound of Formula I(a) with a reducing agent under conditions to provide naltrexone or nalbuphone.

The present invention also includes a method for the preparation of naltrexone, nalbuphone or naloxone from a compound of Formula I(a):

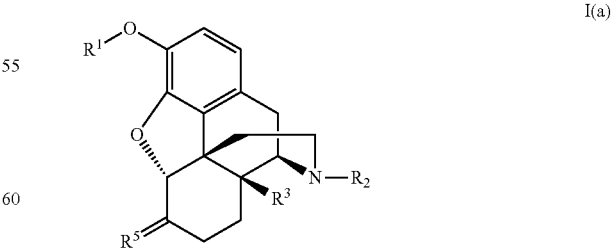

I(a)

wherein $R^1$ is H, $R^3$ is OH, ⚌ is a double bond, $R^5$ is O, $R^2$ is C(O)R$^6$, $R^6$ is selected from C$_{3-10}$cycloalkyl, C$_{3-10}$heterocycloalkyl, C$_{3-10}$cycloalkenyl, C$_{1-20}$alkyl, C$_{2-20}$alkenyl, C$_{2-20}$alkynyl, C$_{6-10}$aryl and C$_{5-10}$heteroaryl, each of the latter eight groups being unsubstituted or substituted with one or more substituents independently selected from $R^7$, $OR^8$, $SiR^7R^{7'}R^8$, $NR^8R^{8'}$, $SR^8$, $S(O)R^7$, $SO_2R^7$, halo, CN and $NO_2$;

$R^7$ and $R^{7'}$ are independently selected from $C_{1-6}$alkyl, $C_{6-10}$aryl and $C_{1-6}$alkylene$C_{6-10}$aryl;

$R^8$ and $R^{8'}$ are independently selected from H, $PG^5$, $C_{1-6}$alkyl, $C_{6-10}$aryl and $C_{1-6}$alkylene$C_{6-10}$aryl, and wherein the compound of Formula I(a) is prepared using the method of the invention, comprising (a) treating the compound of Formula I(a) under deacylating conditions followed by an alkylating reagent of the formula cyclopropyl-CH$_2$-LG, cyclobutyl-CH$_2$-LG or CH$_2$=CH—CH$_2$-LG, wherein LG is a leaving group, under conditions to provide naltrexone, nalbuphone or naloxone, respectively.

The present invention also includes a method for the preparing of buprenorphine from a compound of the Formula I(e):

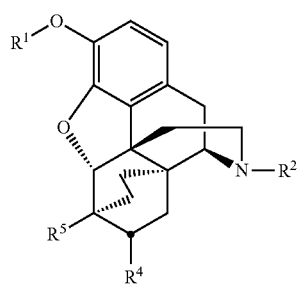

I(e)

wherein $R^1$ is H, $R^4$ is C(Me)(OH)(t-butyl), $R^5$ is OMe, $R^2$ is C(O)cyclopropyl, and the compound of Formula I(e) is prepared using the method the invention, comprising either:

(a) treating the compound of Formula I(e) with a reducing agent under conditions to provide buprenorphine; or (b) treating the compound of Formula I(e) under deacylation conditions followed by an alkylating reagent of the formula cyclopropyl-CH$_2$-LG, wherein LG is a leaving group, under conditions to provide buprenorphine.

The above disclosure generally describes the present invention. It is believed that one of ordinary skill in the art can, using the preceding description, make and use the compositions and practice the methods of the present invention. A more complete understanding can be obtained by reference to the following specific examples. These examples are described solely to illustrate preferred embodiments of the present invention and are not intended to limit the scope of the invention. Changes in form and substitution of equivalents are contemplated as circumstances may suggest or render expedient. Other generic configurations will be apparent to one skilled in the art. All journal articles and other documents such as patents or patent applications referred to herein are hereby incorporated by reference.

EXAMPLES

Although specific terms have been used in these examples, such terms are intended in a descriptive sense and not for purposes of limitation. Methods of chemistry referred to but not explicitly described in the disclosure and these examples are reported in the scientific literature and are well known to those skilled in the art. A list of references is appended and these references are hereby incorporated by reference.

Example 1

General Procedure for Demethylation/Acylation

Tertiary amine (0.1 mmol, 1.0 eq.) was dissolved in acetic anhydride (1 ml) and Pd(OAc)$_2$ (0.01 mmol, 0.1 eq.) added. The reaction was heated at 80° C. for 15 hours, cooled to room temperature and passed through a plug of silica using CHCl$_3$:MeOH:NH$_4$OH 80:20:1 as eluent. The volatiles were removed in-vacuo, and the residue suspended in NaHCO$_3$. The aqueous phase was extracted with CHCl$_3$, and the combined organic extracts washed with 1M HCl and brine before being dried over magnesium sulphate, filtered and the volatiles removed in-vacuo to yield the acyl product.

It will be understood by a person skilled in the art that the above description for Example 1 is provided for the general procedure. The examples shown below in Examples 1a-1j follow the general procedure outlined above, but include the use of different sources of palladium and different amounts of Pd(OAc)$_2$, where applicable, and the use of different solvents, as indicated in the table below.

Examples 1a-j

N-demethylation-acetylation of Hydrocodone

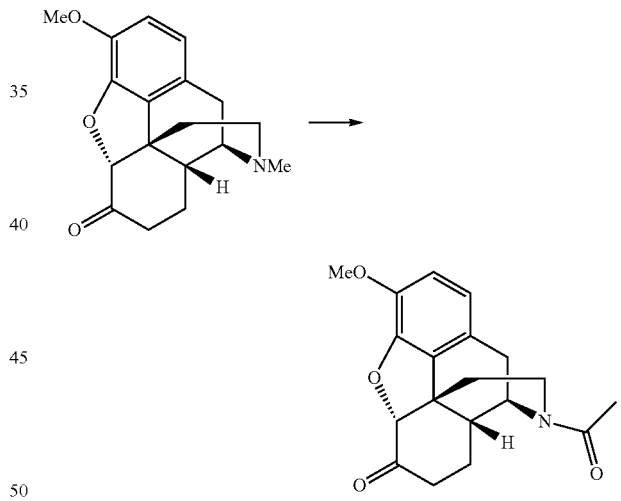

| Example | Conditions (15 hours unless otherwise noted) | Yield % |
|---|---|---|
| 1a | Pd(OAc)$_2$ (1.2 equiv), MeCN, Ac$_2$O, 80° C. | <5% |
| 1b | PdCl$_2$ (1.2 equiv), benzene, Ac$_2$O, 80° C. | 50% |
| 1c | Pd(OAc)$_2$ (0.2 equiv), benzene, Ac$_2$O, 80° C. | 67% |
| 1d | Pd(dba)$_2$ (0.5 equiv), benzene, Ac$_2$O, 80° C. | 76% |
| 1e | Pd(OAc)$_2$ (0.2 equiv), dioxane (dry), Ac$_2$O, 80° C. | 80% |
| 1f | Pd(OAc)$_2$ (0.2 equiv), dioxane (wet), Ac$_2$O, 80° C. | 80% |
| 1g | Pd(OAc)$_2$ (0.2 equiv), toluene, Ac$_2$O, 80° C. | 67% |
| 1h | Pd(OAc)$_2$ (0.2 equiv), MeOH, Ac$_2$O, rt, 3 days | 15% |
| 1i | PdCl$_2$ (0.2 equiv), dioxane, Ac$_2$O, 80° C. | 17.1% |
| 1j | Pd(PPh$_3$)$_4$ (0.2 equiv), dioxane, Ac$_2$O, 80° C. | 76% |
| 1k | Pd(dba)$_2$ (0.2 equiv), dioxane, Ac$_2$O, 80° C. | 72% |

N-Acetyl-N-norhydrocodone was isolated as a mixture of two isomers in a ratio of 3:1 in 80% yield.

(Major isomer) $R_f$ 0.3 (96:4 DCM:MeOH); mp (CHCl$_3$/Hex) 99-100° C.; FTIR ($v_{max}$ cm$^{-1}$) film: 2929, 1727, 1628, 1505, 1436, 1325, 1274, 1241, 1121, 1061, 1026 $^1$H NMR (CDCl$_3$, 600 MHz): 6.77 (d, J=8.2 Hz, 1H), 6.68 (d, J=8.2 Hz, 1H), 5.25-5.28 (m, 1H), 4.69 (s, 1H), 3.94 (s, 3H), 3.67 (dd, J=13.8, 4.8 Hz, 1H), 3.09 (dt, J=13.2, 4.0 Hz, 1H), 2.91 (dd, J=18.6, 6.1 Hz, 1H), 2.67 (d, J=18.5 Hz, 1H), 2.32-2.51 (m, 3H), 2.14 (s, 3H), 1.91-2.02 (m, 3H), 1.20-1.32 (m, 1H) ppm; $^{13}$C NMR (CDCl$_3$, 125 MHz): 206.8, 169.0, 145.6, 143.2, 126.0, 124.9, 120.4, 115.1, 91.0, 56.8, 47.6, 47.3, 41.2, 40.5, 39.9, 35.5, 28.4, 25.3, 22.1 ppm; MS (EI) m/z (%) 327 (24), 241 (23), 117 (10), 87 (68), 86 (21), 85 (72), 84 9 (31), 83 (100), 57 (12), 49 (13), 48 (12), 47 (28), 43 (23), 41 (10); HRMS calc. for C$_{19}$H$_{21}$NO$_4$: 327.1470, found 327.1483.

(Minor isomer) $^1$H NMR (CDCl$_3$, 600 MHz): 6.77 (d, J=8.2 Hz, 1H), 6.67 (d, J=8.2 Hz, 1H), 4.70 (s, 1H), 4.56 (dt, J=14.2, 3.1 Hz, 1H), 4.27-4.31 (m, 1H), 3.94 (s, 3H), 3.67 (dd, J=13.8, 4.8 Hz, 1H), 3.09 (dt, J=13.2, 4.0 Hz, 1H), 2.97 (dd, J=18.2, 5.8 Hz, 1H), 2.76 (d, J=18.1 Hz, 1H), 2.53-2.61 (m, 1H) 2.32-2.51 (m, 2H), 2.14 (s, 3H), 1.91-2.02 (m, 2H), 1.20-1.32 (m, 1H) ppm; $^{13}$C NMR (CDCl$_3$, 125 MHz): 206.7, 168.7, 145.6, 143.6, 126.0, 123.9, 120.3, 115.3, 91.0, 56.8, 53.8, 47.2, 42.1, 39.7, 35.4, 34.7, 29.2, 25.5, 21.9 ppm MS (EI) m/z (%) 327 (24), 241 (23), 117 (10), 87 (68), 86 (21), 85 (72), 84 (31), 83 (100), 57 (12), 49 (13), 48 (12), 47 (28), 43 (23), 41 (10) HRMS calc. for C$_{19}$H$_{21}$NO$_4$: 327.1470, found 327.1483.

Example 2

Reactivity of a Series of Anhydrides

The reactivity of a series of anhydrides was explored following the general procedure outlined in Example 1.

| Example | Anhydride | Time (hrs) | Yield (%) | R |
|---|---|---|---|---|
| 2a | acetic anhydride | 15 | 80 | Me |
| 2b | Cyclopropane-carboxylic anhydride | 24 | 76 | cyclopropyl |
| 2c | iso-butyric anhydride | 24 | 13 | CH(CH$_3$)$_2$ |
| 2d | n-propanoic anhydride | 24 | 53 | Et |
| 2e | decanoic anhydride | 120 | 36 | (CH$_2$)$_8$CH$_3$ |
| 2f | Dodecanoic anhydride | 120 | 43 | (CH$_2$)$_{10}$CH$_3$ |

N-iso-butyryl-norhydrocodone was isolated as a mixture of two isomers in a ratio of 13:4 in 13% yield.

(Major isomer) FTIR ($v_{max}$ cm$^{-1}$) film: 3444, 2970, 2933, 1728, 1643, 1634, 1505, 1435, 1327, 1276, 1260, 1177, 1156, 1032, 958, 754; $^1$H NMR (CDCl$_3$, 300 MHz): 6.77 (d, J=8.2 Hz, 1H), 6.68 (d, J=8.6 Hz, 1H), 5.26-5.33 (m, 1H), 4.68 (s, 1H), 3.94 (s, 3H), 3.74-3.84 (m, 1H), 2.73-3.12 (m, 3H), 2.62 (d, J=18.5 Hz, 1H), 2.28-2.51 (m, 3H), 1.87-2.06 (m, 3H), 1.20-1.30 (m, 1H), 1.19 (d, J=6.8 Hz, 3H), 1.12 (d, J=7.02 Hz, 3H); $^{13}$C NMR (CDCl$_3$, 75.5 MHz): 206.92, 175.35, 145.57, 143.18, 126.18, 125.08, 120.36, 115.13, 90.97, 56.78, 47.61, 47.39, 41.38, 39.92, 39.35, 35.86, 30.46, 28.45, 25.35, 19.62, 19.08; MS (EI) m/z (%): 355 (34.5), 242 (12.5), 241 (33.7), 115 (98.6), 100 (12.5), 88 (12.7), 87 (16.0), 86 (65.9), 84 (100.0), 72 (23.7), 55 (10.7), 49 (19.5), 47 (23.7), 43 (52.9), 41 (15.1); HRMS (EI) calcd for C$_{21}$H$_{25}$NO$_4$: 355.1784; found 355.1777.

Cyclopropylcarbonyl-nor-hydrocodone was isolated as a mixture of two isomers in a ratio of 3:1 in 76% yield.

FTIR ($v_{max}$ cm$^{-1}$) film: 3448, 3007, 2929, 1728, 1631, 1505, 1438, 1327, 1275, 1115, 960, 753 (Major isomer) $^1$H NMR (CDCl$_3$, 600 MHz): 6.76 (d, J=8.2 Hz, 1H), 6.64-6.70 (m, 1H), 5.22-5.26 (m, 1H), 4.69 (s, 1H), 4.09 (dd, J=13.7, 4.6 Hz, 1H), 3.92 (s, 3H), 3.12 (dt, J=13.2, 3.7 Hz, 1H), 2.89 (dd, J=18.3, 6.2 Hz, 1H), 2.65 (d, J=18.5 Hz, 1H), 2.31-2.63 (m, 5H), 2.04 (dt, J=12.5, 5.1 Hz, 1H), 1.89-2.00 (m, 1H), 1.70-1.78 (m, 1H), 1.18-1.36 (m, 1H), 0.96-1.09 (m, 1H), 0.74-0.92 (m, 2H) $^{13}$C NMR (CDCl$_3$, 150 MHz): 207.1, 172.0, 145.6, 143.3, 126.2, 125.1, 120.4, 115.1, 91.1, 67.1, 56.7, 48.3, 47.4, 42.1, 39.9, 36.2, 29.7, 28.4, 11.5, 8.8, 7.6 (Minor isomer) $^1$H NMR (CDCl$_3$, 600 MHz): 6.76 (d, J=8.2 Hz, 1H), 6.64-6.70 (m, 1H), 4.73-4.77 (m, 1H), 4.70 (s, 1H), 4.50 (dd, J=13.9, 3.6 Hz, 1H), 3.92 (s, 3H), 2.99 (dd, J=18.0, 5.7 Hz, 1H), 2.80 (d, J=18.1 Hz, 1H), 2.31-2.63 (m, 5H), 2.04 (dt, J=12.5, 5.1 Hz, 1H), 1.89-2.00 (m, 1H), 1.81-1.83 (m, 1H), 1.57-1.65 (m, 1H), 1.18-1.36 (m, 1H), 0.96-1.09 (m, 1H), 0.74-0.92 (m, 2H) $^{13}$C NMR (CDCl$_3$, 150 MHz): 206.9, 171.9, 145.5, 143.1, 126.2, 125.1, 120.2, 114.9, 91.0, 67.1, 56.7, 48.3, 47.4, 41.2, 39.7, 35.7, 29.4, 25.3, 11.5, 7.5, 7.3 MS (EI) m/z (%): 354 (17), 353 (66), 301 (28), 300 (11), 242 (30), 241 (57), 240 (14), 213 (11), 199 (11), 185 (19), 164 (30), 141 (10), 129 (16), 128 (12), 127 (10), 115 (15), 114 (11), 113 (61), 112 (82), 111 (28), 109 (11), 99 (11), 98 (73), 97 (11), 88 (23), 87 (19), 86 (48), 85 (89), 84 (80), 83 (100), 82 (18), 72 (13), 71 (21), 70 (25), 69 (81), 68 (14), 60 (12), 59 (18), 58 (22), 57 (37), 56 (13), 55 (31), 49 (21), 48 (13), 47 (36), 45 (22), 44 (28), 43 (40), 42 (32), 41 (77) HRMS (EI) calcd for C$_{21}$H$_{23}$NO$_4$: 353.1627; found 353.1612.

N-n-propionyl-norhydrocodone was isolated as a mixture of two isomers in a ratio of 3:1 in 53% yield.

(Major isomer) FTIR ($v_{max}$ cm$^{-1}$) film: 3436, 2918, 2849, 1727, 1634, 1505, 1437, 1276, 1118, 1031, 971 $^1$H NMR (CDCl$_3$, 600 MHz): 6.68 (d, J=8.2 Hz, 1H), 6.59 (d, J=8.3 Hz, 1H), 5.17-5.22 (m, 1H), 4.60 (s, 1H), 3.85 (s, 3H), 3.62 (dd, J=13.4, 5.0 Hz, 1H), 2.96 (dt, J=13.0, 3.8 Hz, 1H), 2.83 (dd, J=18.6, 6.0 Hz, 1H), 2.56 (d, J=8.5 Hz, 1H), 2.20-2.47 (m, 6H), 1.81-1.93 (m, 3H), 1.10 (t, J=7.7 Hz, 3H); $^{13}$C NMR (CDCl$_3$, 125 MHz): 206.9, 172.3, 145.6, 143.3, 126.2, 125.2, 120.5, 115.2, 91.1, 56.8, 47.9, 47.3, 41.4, 40.1, 39.5, 35.9, 28.5, 27.2, 25.4, 9.7; MS (EI) m/z (%): 341 (33.1), 242 (12.2), 241 (30.6), 188 (11.1), 185 (11.0), 167 (10.8), 149 (28.3), 129 (13.2), 113 (10.0), 102 (11.2), 101 (100.0), 72 (17.6), 71 (13.6), 70 (13.5), 57 (85.0), 56 (10.7), 55 (19.3), 43 (18.2), 41 (13.8) HRMS (EI) calcd for C$_{20}$H$_{23}$NO$_4$: 341.1627; found 341.1628.

N-n-decanoyl-norhydrocodone was isolated as a mixture of two isomers in a ratio of 3:1 in 36% yield.

(Major isomer) FTIR ($v_{max}$ cm$^{-1}$) film: 3435, 2926, 2850, 1726, 1626, 1505, 1436, 1155, 1030, 892, 753; $^1$H NMR (CDCl$_3$, 600 MHz): 6.68 (d, J=8.2 Hz, 1H), 6.59 (d, J=8.0 Hz, 101H), 5.18-5.21 (m, 1H), 4.60 (s, 1H), 3.84 (s, 3H), 3.62 (dd, J=13.5, 4.6 Hz, 1H), 3.38 (m, 1H), 2.96 (dt, J=13.1, 3.8 Hz, 1H), 2.83 (dd, J=18.6, 6.1 Hz, 1H), 2.55 (d, J=18.4 Hz, 1H), 2.34-2.40 (m, 1H), 2.20-2.33 (m, 3H), 1.81-1.93 (m, 2H), 1.59-1.65 (m, 2H), 1.49-1.58 (m, 2H), 1.13-1.33 (m, 12), 0.81 (t, J=6.8 Hz, 3H); $^{13}$C NMR (CDCl$_3$, 125 MHz): 207.3, 171.9, 145.6, 143.4, 126.2, 124.9, 120.7, 115.1, 91.3, 56.7, 47.4, 41.3, 39.9, 39.7, 35.7, 34.0, 33.8, 31.9, 31.7, 29.5, 29.4, 28.4, 25.6, 25.4, 25.0, 22.7, 14.1; MS (EI) m/z (%): 439 (1.0), 224 (41.8), 172 (10.1), 143 (36.3), 100 (15.8), 99 (56.6), 98 (36.9), 83 (18.2), 82 (11.2), 70 (21.3), 67 (10.4), 61 (52.2), 57 (19.3), 56 (100.0), 55 (43.2), 44 (14.1), 43 (46.5), 41 (42.7); HRMS (EI) calcd for C$_{27}$H$_{37}$NO$_4$: 439.2723; found 439.2719.

N-n-dodecanoyl-norhydrocodone was isolated as a mixture of two isomers in a ratio of 3.6:1 in 43% yield.

(Major isomer) FTIR ($v_{max}$ cm$^{-1}$) film: 3334, 2926, 2852, 1729, 1627, 1575, 1505, 1438, 1275, 1031, 965; $^1$H NMR (CDCl$_3$, 300 MHz): 6.77 (d, J=8.2 Hz, 1H), 6.67 (d, J=8.5 Hz, 1H), 5.24-5.32 (m, 1H), 4.69 (s, 1H), 3.93 (s, 3H), 3.66-3.76 (m, 1H), 3.42-3.58 (m, 1H), 2.98-3.11 (m, 1H), 2.91 (dd, J=18.6, 6.1 Hz, 1H), 2.63 (d, J=18.5 Hz, 1H), 2.23-2.52 (m, 3H), 1.87-2.04 (m, 4H), 1.54-1.79 (m, 4H), 1.20-1.47 (m, 15H), 1.01-1.20 (m, 3H), 0.89 (t, J=6.5 Hz, 3H); $^{13}$C NMR (CDCl$_3$, 75.5 MHz): 207.2, 171.8, 145.9, 143.3, 126.2, 125.2, 120.5, 115.2, 91.1, 56.8, 49.4, 47.6, 47.4, 41.4, 39.8, 35.9, 35.7, 34.2, 34.0, 32.1, 32.0, 29.7, 29.6, 29.5, 25.8, 25.4, 25.0, 22.8, 14.3; MS (EI) m/z (%): 467 (2.5), 224 (21.4), 143 (17.6), 100 (10.0), 99 (27.0), 98 (17.4), 61 (23.2), 56 (100.0), 55 (19.9), 43 (20.5), 41 (19.1); HRMS (EI) calcd for C$_{29}$H$_{41}$NO$_4$: 467.3036; found 467.3037.

Example 3

N-acylation of Tropane Alkaloids

The above procedure outlined in Examples 1 and 2 was also applied to other N-methylated heterocycles, identified below in Examples 3a-3e.

Examples 3a-3e

| Example | Substrate | Conditions Pd(OAc)$_2$ 0.2 equiv. | Isolated yield % (conversion % by GCMS) |
|---|---|---|---|
| 3a | Me-N bicyclic ketone | a) Ac$_2$O neat, 80° C., 14 hrs; b) PhH, Ac$_2$O, 80° C., 60 hrs; | Ac-N bicyclic ketone; a) 72% (100%); b) 48% (60%); |
| 3b | Me-N bicyclic | Ac$_2$O neat, 80° C., 14 hrs | Ac-N bicyclic; 70% (100%) |
| 3c | Me-N bicyclic alcohol (OH) | Ac$_2$O neat, 80° C., 14 hrs | Ac-N bicyclic OAc 43%; Me-N bicyclic OAc 35% |
| 3d | Me-N tropane tropate ester (HO, Ph) | benzene, Ac$_2$O, 80° C., 14 hrs | Ac-N tropane with acrylate-Ph; 85% |

| Example | Substrate | Conditions Pd(OAc)₂ 0.2 equiv. | Isolated yield % (conversion % by GCMS) |
|---|---|---|---|
| 3e | 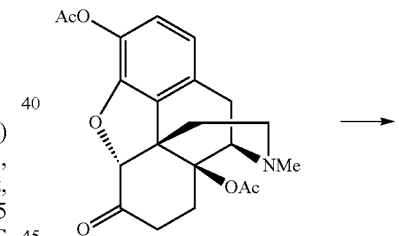 | 10 equiv. succinic anhydride, benzene, 80° C., 60 hrs, (1 equiv of Pd(OAc)₂ used) | 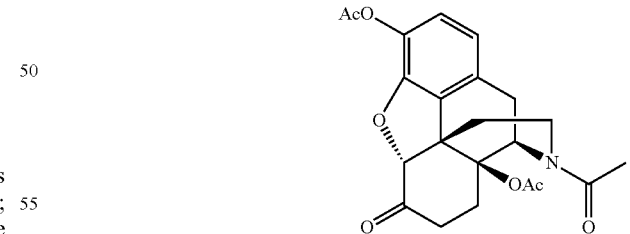 10% (50%) |

8-acetyl-8-aza-bicyclo[3.2.1]octan-3-yl 2-phenylacrylate $R_f$ 0.3 (96:4 DCM:MeOH); mp 104-107° C.; FTIR ($v_{max}$ cm$^{-1}$) film: 2953, 2922, 1714, 1635, 1495, 1445, 1424, 1327, 1196, 1167, 1076, 1034; $^1$H NMR (CDCl₃, 300 MHz): 7.29-7.42 (m, 5H), 6.37 (s, 1H), 5.89 (s, 1H), 5.25 (t, J=4.8 Hz, 1H), 4.59-4.68 (m, 1H), 4.04-4.13 (m, 1H), 2.22 (dt, J=15.3, 4.3 Hz, 1H), 2.05 (s, 3H), 1.78-2.15 (m, 7H) ppm; $^{13}$C NMR (CDCl₃, 75.5 MHz): 166.1, 165.8, 141.8, 136.7, 123.3, 128.2, 128.1, 127.0, 68.3, 54.2, 50.1, 37.3, 35.6, 28.6, 26.9, 21.5 ppm; MS (EI) m/z (%) 299 (18), 257 (16), 168 (15), 152 (28), 151 (32), 136 (18), 126 (10), 111 (14), 110 (100), 109 (38), 108 (17), 103 (38), 97 (10), 86 (27), 84 (44), 83 (15), 82 (19), 81 (25), 80 (29), 77 (22), 71 (11), 69 (33), 68 (35) 67 (28), 57 (19), 55 (18), 47 (10), 43 (68), 41 (26); HRMS (EI) calcd for $C_{18}H_{21}NO_3$: 299.1521; found 299.1518; Anal. calcd for $C_{18}H_{21}NO_3$: C, 72.22%; H, 7.07%. found: C, 70.84%; H, 7.18%.

4-oxo-4-(3-oxo-8-aza-bicyclo[3.2.1]octan-8-yl)butanoic acid $R_f$ 0.3 (96:4:1 DCM:MeOH:AcOH); FTIR ($v_{max}$ cm$^{-1}$) film: 3416, 2959, 2924, 2852, 2645, 1715, 1618, 1459, 1413, 1199, 1178; $^1$H NMR (CDCl₃, 300 MHz): 4.95 (t, J=5.8 Hz, 1H), 4.52 (t, J=5.7 Hz, 1H), 2.65-2.94 (m, 6H), 2.43 (t, J=16.5 Hz, 2H), 2.00-2.29 (m, 2H), 1.65-1.92 (m, 2H) ppm; $^{13}$C NMR (CDCl₃, 75.5 MHz): 207.1, 176.7, 168.4, 53.7, 51.4, 49.4, 49.8, 29.9, 29.0, 28.3, 27.7 ppm.

Example 4

Substitution of the Anhydride With Dimethyldicarbonate

Hydrocodone bitartrate (100 mg, 0.22 mmol, 1 eq.) was suspended in a mixture of benzene and dimethyldicarbonate; 1:1 (2 mL) and Pd(OAc)₂ was added. The reaction mixture was heated to 80° C. for 18 hrs, before it was cooled to rt and filtered through a plug of celite. The solvent was evaporated and the residue was taken up in CHCl₃ and the organic layer was washed with 1N HCl. The organic layer was dried over MgSO₄, the solvent was evaporated and the residue was purified by flash column chromatography (CHCl₃:MeOH; 100:0→90:10) to give 25 mg of compound 8 as a mixture of 2 isomers in a ratio of 6:4 (33%) as colorless oil.

$R_f$ 0.55 (92:8; DCM:MeOH); FTIR ($v_{max}$ cm$^{-1}$) film: 3019, 2955, 2934, 2842, 2806, 1744, 1637, 1610, 1506, 1441, 1325, 1263, 1164, 1040; $^1$H NMR (CDCl₃, 600 MHz): 6.75 (d, J=8.2 Hz, 2H), 6.63-6.68 (m, 2H), 4.77-4.81 (m, 1H), 4.67-4.70 (m, 2H), 4.60-4.64 (m, 1H), 4.10 (dd, J=13.5, 5.0 Hz, 1H), 3.93-3.98 (m, 1H), 3.92 (s, 6H), 3.80-3.88 (m, 2H), 3.76 (s, 3H), 3.73 (s, 3H), 2.83-2.91 (m, 2H), 2.75-2.82 (m, 2H), 2.68-2.74 (m, 2H), 2.42-2.48 (m, 4H), 2.34-2.41 (m, 2H), 1.82-2.00 (m, 4H), 1.18-1.28 (m, 2H) ppm; $^{13}$C NMR (CDCl₃, 125 MHz): 207, 2, 155, 9, 155.5, 145.5, 143.1, 126.1, 124.9, 124.7, 120.4, 120.3, 114.9, 114.8, 91.2, 56.7, 52.9, 52.8, 50.9, 50.6, 47.24, 47.17, 41.5, 41.4, 40.7, 39.9, 39.8, 38.01, 37.97, 35.0, 34.8, 28.9, 28.5, 25.4, 25.3 ppm; HRMS (EI) calc. for $C_{19}H_{21}NO_5$: 343.1420, found: 343.1421.

Example 5

N-demethylation/acylation of Protected Oxymorphone

Mixture of 14-acetyl oxymorphone (0.077 g; 0.2 mmol), Pd(OAc)₂ (0.0045 g; 0.02 mmol), acetic anhydride (0.8 mL) and dioxane (0.8 mL) was stirred at 80° C. under air for 18 h. When the starting material disappeared the mixture was evaporated to dryness under high-vacuum, diluted with dichloromethane (10 mL) and washed with sat. NaHCO₃ (3 mL). The aqueous layer was re-extracted with dichloromethane (3×5 mL) and the combined organic layers were washed with water, brine, dried over Na₂SO₄ and concentrated. Chromatography (eluent EtOAc+10% MeOH) afforded 0.078 g (95%) of white solid, consisting of a 1:2 mixture of axial and equatorial amide isomers of 3,14,17-triacetylnoroxymorphone; mp>235° C. (EtOH); $R_f$ 0.44 (ethyl acetate+10% methanol; IR (CHCl₃) v 3027, 3011, 2931, 1761, 1733, 1634, 1444, 1370, 1157, 1053 cm⁻¹;

Major isomer: ¹H NMR (600 MHz, CDCl₃) δ 6.94 (d, J=8.1 Hz, 1H), 6.74 (d, J=8.1 Hz, 1H), 5.34 (d, J=5.6 Hz, 1H), 4.73 (s, 1H), 4.54 (dd, J=14.1, 5.3 Hz, 1H), 3.20 (dd, J=18.5, 5.9 Hz, 1H), 3.03-2.90 (m, 2H), 2.60-2.52 (m, 2H), 2.43 (ddd, J=12.7, 12.7, 5.6 Hz, 1H), 2.35 (m, 1H), 2.34 (s, 3H), 2.20 (s, 3H), 2.14 (s, 3H), 1.72-1.62 (m, 2H); ¹³C NMR (150 MHz, CDCl₃) δ 205.03, 170.79, 170.14, 168.24, 147.47, 133.16, 128.88, 127.91, 124.07, 119.93, 89.90, 81.23, 53.50, 50.65, 35.14, 34.22, 32.75, 28.24, 26.01, 22.04, 21.46, 20.77;

Minor isomer: ¹H NMR (600 MHz, CDCl₃) δ 6.92 (d, J=8.1 Hz, 1H), 6.76 (d, J=8.1 Hz, 1H), 6.07 (d, J=5.8 Hz, 1H), 4.72 (s, 1H), 3.65 (dd, J=13.9, 5.1 Hz, 1H), 3.17-3.10 (m, 2H), 3.08 (dd, J=13.5, 3.9 Hz, 1H) 2.97 (m, 1H), 2.57-2.48 (m, 2H), 2.34 (s, 3H), 2.31 (m, 2H), 2.14 (s, 3H), 2.14 (s, 3H), 2.12 (s, 3H), 1.72-1.62 (m, 2H); ¹³C NMR (150 MHz, CDCl₃) δ 205.33, 169.53, 169.44, 168.37, 147.91, 132.99, 129.83, 128.00, 123.90, 120.11, 89.81, 80.74, 48.13, 50.75, 39.37, 35.17, 31.85, 28.98, 26.11, 22.00, 21.87, 20.77; MS (+EI) m/z (%): 43 (100), 311 (45), 329 (3), 371 (6), 413 (3); HRMS calcd for C₂₂H₂₃NO₇ 413.1475, found 413.14793.

The examples 5a-p provided below follow the general procedure identified above,

Examples 5a-5p

N-Demethylation/acylation of 14-acetyl oxymorphone

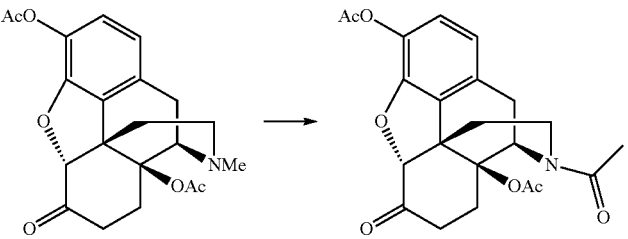 [SMILES: CC(=O)Oc1ccc2c3c1O[C@H]1C(=O)CC[C@@]4(OC(C)=O)[C@@H](C2)N(C)CC[C@]314 ; CC(=O)Oc1ccc2c3c1O[C@H]1C(=O)CC[C@@]4(OC(C)=O)[C@@H](C2)N(C(C)=O)CC[C@]314]

Example 6

Preparation of Noroxymorphone

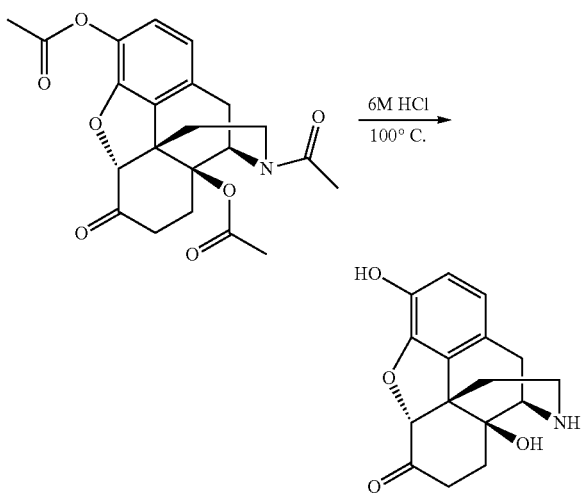

A mixture of the 3,14,17-triacetylnoroxymorphone (0.65 g; 1.57 mmol) and 6 molar HCl (9 mL) was stirred at 100° C. for 3 h. Then the mixture was allowed to cool to room temperature (precipitation of crystals was observed) and the pH was carefully adjusted to 8-9 by addition of 20% NaOH solution. The resulting mixture was stirred for 1 h and then the fine suspension was filtered through a frit funnel. The filtration cake was washed with distilled water, suspended in methanol and brought to reflux. The crystalline material was

| Entry | Conditions | Ac₂O (eq.) | Catalyst/mol % | Co-cat/mol % | Yield (%) |
|---|---|---|---|---|---|
| 5a | Dioxane, 80° C., 48 h, AIR | co-solv. | Pd(acac)₂/1 | None | 75 |
| 5b | Dioxane, 80° C., 14 h, AIR | co-solv. | Pd(acac)₂/10 | CuCl₂/10 | 0 |
| 5c | Dioxane, 80° C., 5 h, AIR | co-solv. | Pd(OAc)₂/10 | Cu(OAc)₂/10 | 90 |
| 5d | Dioxane, 45° C., 24 h, AIR | co-solv. | Pd(acac)₂/10 | CuCl₂/10 | 0 |
| 5e | Dioxane, 80° C., 5 h, AIR | co-solv. | Pd(OAc)₂/5 | Cu(OAc)₂/5 | 90 |
| 5f | Dioxane, 80° C., 5 h, AIR | 15 | Pd(OAc)₂/5 | Cu(OAc)₂/5 | 92 |
| 5g | Dioxane, 80° C., 17 h, AIR | co-solv. | None | Cu(acac)₂/10 | 0 |
| 5h | Dioxane, 80° C., 5 h, AIR | 10 | Pd(OAc)₂/5 | Cu(OAc)₂/5 | 88 |
| 5i | Dioxane, 80° C., 4 h, O₂ | 15 | Pd(OAc)₂/5 | Cu(OAc)₂/5 | 90ᵃ |
| 5j | Dioxane, 80° C., 16 h, K₃[Fe(CN)₆] | co-solv. | Pd(OAc)₂/10 | None | 0 |
| 5k | Dioxane, 80° C., 20 h, O₂ | 15 | Pd(OAc)₂/10 | None | 90ᵃ |
| 5l | Dioxane, 80° C., 5.5 h, O₂ | 15 | Pd(acac)₂/5 | None | 90 |
| 5m | Dioxane, 80° C., 3.5 h, O₂ | 15 | Pd(OAc)₂/5 | None | 95 |
| 5n | Dioxane, 80° C., 22 h, O₂ | 15 | Pd black/10 | None | 80 |
| 5o | Dioxane, 80° C., 22 h, Argon | 15 | Pd(OAc)₂/5 | Cu(OAc)₂/200 | 24 |
| 5p | Dioxane, 80° C., 4.5 h, O₂ | 5 | Pd(OAc)₂/5 | none | 90 | filtered and dried under vacuum at 80° C. overnight to provide 0.40 g (90%) of the titled compound as a white solid.

mp>230° C. (MeOH); [α]$^{20}_D$=−172.5 (c=1, AcOH); $^1$H NMR (600 MHz, DMSO) δ 6.57 (d, J=8.0 Hz, 1H), 6.52 (d, J=8.0 Hz, 1H), 5.32 (bs, 1H), 4.69 (s, 1H), 2.99 (m, 1H), 2.96-2.83 (m, 3H), 2.63 (dd, J=13.0, 3.9 Hz, 1H), 2.37 (ddd, J=13.0, 13.0, 2.8 Hz 1H), 2.30 (ddd, J=12.0, 12.0, 4.5 Hz, 1H), 2.07 (m, 1H), 1.73 (s, 1H), 1.45 (ddd, J=14.0, 14.0, 2.8 Hz, 1H), 1.17 (m, 1H); $^{13}$C NMR (150 MHz, DMSO) δ 209.22, 143.93, 139.85, 129.93, 124.27, 119.44, 117.66, 89.98, 70.07, 57.31, 50.85, 37.84, 36.29, 31.81, 31.80, 29.95; MS (+EI) m/z (%): 44 (13), 56 (13), 126 (20), 174 (15), 202 (34), 242 (5), 259 (5), 287 (100); HRMS calcd for $C_{16}H_{17}NO_4$ 287.1158. found 287.1154.

Example 7

N-Alkylation of Noroxymorphone

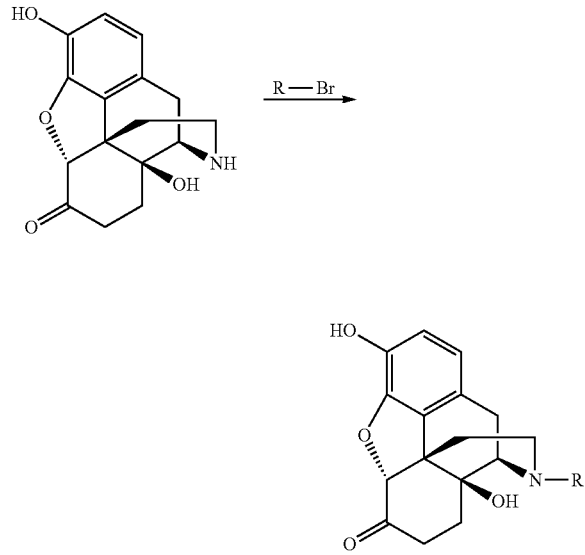

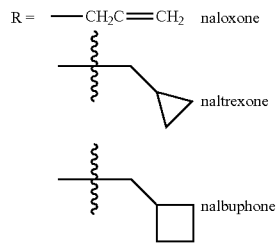

To a solution of noroxymoprphone (Example 6, 1 eq.) in N-methylpyrrolidine is added NaHCO$_3$ (1.2 eq) and finally cyclopropylmethyl bromide (1.25 eq). The reaction mixture is placed into a pre-heated oil bath at 85° C. and stirred for 18 h. After this time it is diluted with water, extracted three times with EtOAc and the combined organic layers are washed with water, brine, dried over Na$_2$SO$_4$ and concentrated. Column chromatography may be used to purify the N-alkylated products.

Example 8

[5α,7α]-(1,1-Dimethylethyl)-4,5-epoxy-18,19-dihydro-3,6-dimethoxy-α,17-dimethyl-6,14-ethenomorphinan-7-methanol

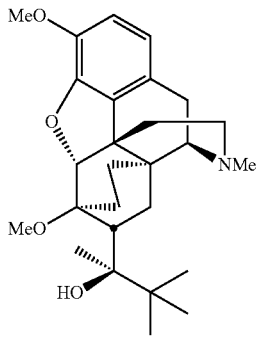 [SMILES: COc1ccc2c3c1O[C@H]1[C@@]4(OC)CC[C@@]5(C[C@@H]4[C@](C)(O)C(C)(C)C)[C@@H](C2)N(C)CC[C@]315]

This intermediate was prepared according to literature methods described in (a) Bentley, K. W; U.S. Pat. No. 3,433,791 (1969); and (b) Allen, B. E.; Jarvi, E. T.; Kalota, D. J.; Meyer, J. R.; Tomazi, K. G.; Mannini, A.; Orr, B.; US 2010/0087647.

mp 186-188° C. (EtOH); R$_f$ 0.46 (ethyl acetate); [α]$^{20}_D$=−107.24 (c=1, CHCl$_3$); IR (CHCl$_3$) v 3384, 2980, 2840, 1630, 1502, 1453, 1130, 1080, 941 cm$^{-1}$; $^1$H NMR (600 MHz, CDCl$_3$) δ 6.72 (d, J=8.1 Hz, 1H), 6.59 (d, J=8.1 Hz, 1H), 5.96 (s, 1H, OH), 4.44 (d, J=1.4 Hz, 1H), 3.89 (s, 3H), 3.58 (s, 3H), 3.13 (d, J=18.4 Hz, 1H), 2.82 (ddd, J=13.2, 13.2, 3.8 Hz, 1H), 2.65 (d, J=6.3 Hz, 1H), 2.44 (dd, J=11.9, 5.3 Hz, 1H), 2.31 (s, 3H), 2.29 (dd, J=12.3, 3.8 Hz, 1H), 2.23 (dd, J=18.4, 6.4 Hz, 1H), 2.17 (dd, J=9.8, 9.8 Hz, 1H), 1.99 (ddd, J=12.7, 12.7, 5.6 Hz, 1H), 1.86 (m, 1H), 1.78 (ddd, J=12.7, 12.7, 5.7 Hz, 1H), 1.69 (dd, J=12.9, 12.9, 2.6 Hz, 1H), 1.37 (s, 3H), 1.34 (dd, J=13.2, 9.1 Hz, 1H), 1.09 (m, 1H), 1.05 (s, 9H), 0.76 (m, 1H); $^{13}$C NMR (150 MHz, CDCl$_3$) δ 146.87, 141.67, 132.71, 128.93, 119.13, 114.03, 96.59, 80.65, 79.43, 61.38, 56.85, 52.57, 45.43, 45.12, 43.60, 43.52, 40.41, 36.01, 35.56, 33.36, 29.65, 26.44, 21.97, 20.26, 18.19; MS (FAB+) m/z (%): 44 (14), 101 (17), 352 (32), 384 (36), 424 (57), 442 (100); HRMS calcd for $C_{27}H_{40}NO_4$ 442.2952, found 442.29854.

Example 9

1-[(5α,7α)-3-methoxy-4,5-epoxy-18,19-dihydro-7-[(1S)-1-hydroxy-1,2,2-trimethylpropyl]-6-methoxy-6,14-ethenomorphinan-17-yl]-ethanone

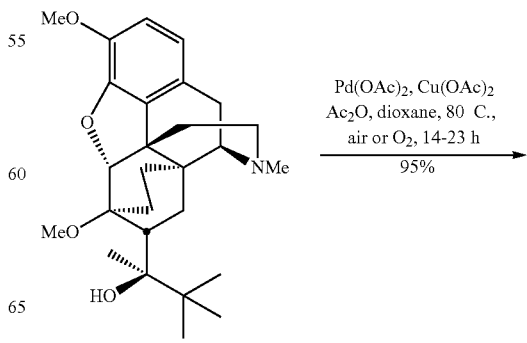

-continued

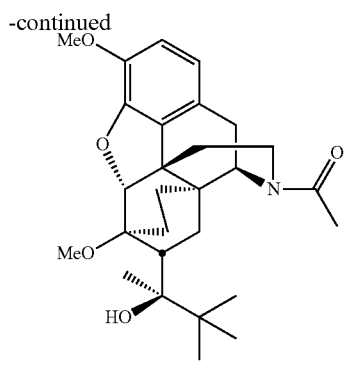

A mixture of [5α,7α]-(1,1-dimethylethyl)-4,5-epoxy-18, 19-dihydro-3,6-dimethoxy-α,17-dimethyl-6,14-ethenomorphinan-7-methanol (Example, 1, 0.088 g; 0.2 mmol), Pd(OAc)$_2$ (0.0022 g; 0.01 mmol), Cu(OAc)$_2$ (0.002 g; 0.01 mmol), acetic anhydride (0.3 g; 3.0 mmol) and dioxane (1 mL) was stirred at 80° C. for 23 h. Then the mixture was evaporated to a thick oil and diluted with dichloromethane (5 mL). The resulting mixture was washed with saturated solution of NaHCO$_3$ (10 mL) and the aqueous layer was extracted with dichloromethane (3×3 mL). Combined organic layers were washed with water, brine, dried over Na$_2$SO$_4$ and concentrated. Column chromatography (eluent EtOAc) afforded 0.09 g (95%) of the title compound; ratio of isomers 1:1.5; mp 155-159° C. (EtOH, mixture of isomers); R$_f$ 0.51 (ethyl acetate); IR (CHCl$_3$) ν 3396, 3001, 2840, 1628, 1503, 1441, 1163, 1080, 908 cm$^{-1}$; major isomer: $^1$H NMR (600 MHz, CDCl$_3$) δ 6.77 (d, J=8.1 Hz, 1H), 6.62 (d, J=8.1 Hz, 1H), 5.79 (s, 1H, OH), 4.87 (d, J=6.9 Hz, 1H), 4.44 (s, 1H), 3.90 (s, 3H), 3.64 (dd, J=14.1, 5.1 Hz, 1H), 3.56 (s, 3H), 3.34 (ddd, J=13.4, 13.4, 3.0 Hz, 1H), 2.89 (m, 1H), 2.74 (d, J=18.7 Hz, 1H), 2.15 (s, 3H), 2.08 (m, 1H), 1.99 (m, 1H), 1.96-1.82 (m, 3H), 1.78 (m, 1H), 1.52 (dd, J=12.3, 10.0 Hz, 1H), 1.34 (s, 3H), 1.23 (m, 2H), 0.99 (s, 9H), 0.73 (m, 1H); $^{13}$C NMR (150 MHz, CDCl$_3$) δ 168.75, 147.05, 142.14, 131.37, 126.95, 119.85, 114.64, 96.40, 80.36, 79.19, 56.79, 52.70, 49.59, 46.17, 43.92, 40.29, 38.74, 35.01, 32.85, 32.61, 32.05, 28.66, 26.42, 21.56, 20.07, 17.80;

Minor isomer: $^1$H NMR (600 MHz, CDCl$_3$) δ 6.77 (d, J=8.1 Hz, 1H), 6.62 (d, J=8.1 Hz, 1H), 5.80 (s, 1H, OH), 4.57 (dd, J=14.1, 5.2 Hz, 1H), 4.45 (s, 1H), 3.90 (s, 3H), 3.85 (d, J=6.6 Hz, 1H), 3.56 (s, 3H), 3.01-2.92 (m, 2H), 2.79 (m, 1H), 2.20-2.12 (m, 2H), 2.12 (s, 3H), 1.96-1.82 (m, 3H), 1.78 (m, 1H), 1.44 (dd, J=9.6, 6.6 Hz, 1H), 1.36 (s, 3H), 1.18 (m, 1H), 0.99 (s, 9H), 0.78 (m, 1H); $^{13}$C NMR (150 MHz, CDCl$_3$) δ 168.67, 147.05, 142.24, 131.43, 126.22, 119.72, 114.76, 96.11, 80.20, 79.12, 56.85, 56.06, 52.73, 46.01, 43.42, 40.41, 36.02, 35.45, 33.99, 33.44, 32.64, 29.13, 26.38, 21.70, 20.07, 18.01

MS (+EI) m/z (%): 43 (29), 57 (14), 84 (100), 352 (33), 380 (100), 394 (45), 412 (87), 469 (2); HRMS calcd for C$_{28}$H$_{39}$NO$_5$ 469.2828, found 469.28324.

Example 10

[5α,7α]-α-(1,1-dimethylethyl)-4,5-epoxy-18,19-dihydro-3,6-dimethoxy-α-methyl-6,14-ethenomorphinan-7-methanol

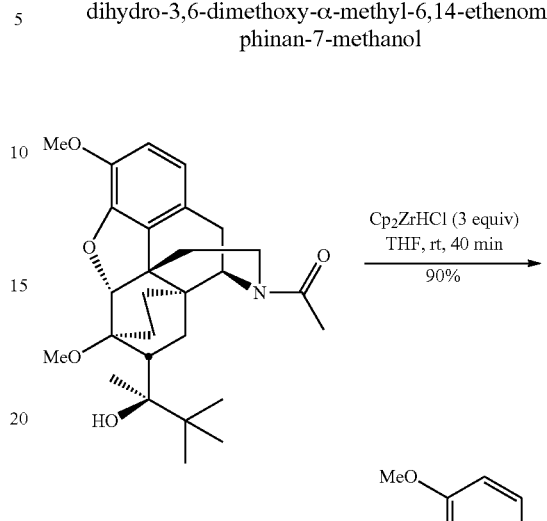

To the solution of 1-[(5α,7α)-3-methoxy-4,5-epoxy-18, 19-dihydro-7-[(1S)-1-hydroxy-1,2,2-trimethylpropyl]-6-methoxy-6,14-ethenomorphinan-17-yl]-ethanone (Example 2, 0.16 g; 0.34 mmol) in THF (4 mL) at room temperature was added the Schwartz's reagent (0.263 g; 1.02 mmol) in one portion. The resulting suspension was stirred under argon atmosphere for 40 min, at which time the suspension turned pale red. The reaction mixture was evaporated to a thick oil which was loaded onto a column. Chromatography (eluent dichloromethane+10% MeOH) afforded 0.13 g (90%) of the titled compound as a white solid; mp 169-171° C. (EtOH); R$_f$ 0.44 (dichloromethane+10% methanol); [α]$^{20}_D$=−99.04 (c=1.0, CHCl$_3$); IR (CHCl$_3$) ν 3384, 2975, 2838, 1628, 1598, 1503, 1454, 1164 cm$^{-1}$; $^1$H NMR (600 MHz, CDCl$_3$) δ 6.74 (d, J=8.1 Hz, 1H), 6.59 (d, J=8.1 Hz, 1H), 5.94 (s, 1H, OH), 4.42 (d, J=1.7 Hz, 1H), 3.89 (s, 3H), 3.56 (s, 3H), 3.00-2.92 (m, 2H), 2.92-2.88 (m, 2H), 2.79 (dd, J=13.0, 4.8 Hz, 1H), 2.65 (ddd, J=12.1, 12.1, 3.9 Hz, 1H), 2.19 (dd, J=9.9, 9.6 Hz, 1H), 1.92-1.84 (m, 2H), 1.83-1.76 (m, 2H), 1.67 (dd, J=13.0, 3.0 Hz, 1H), 1.40 (dd, J=13.0, 9.0 Hz, 1H), 1.37 (s, 3H), 1.09 (ddd, J=12.6, 12.6, 6.1 Hz, 1H), 1.05 (s, 9H), 0.72 (dddd, J=12.6, 12.6, 3.6, 3.6 Hz, 1H); $^{13}$C NMR (150 MHz, CDCl$_3$) δ 146.91, 141.77, 132.55, 128.80, 119.17, 114.08, 96.97, 80.45, 79.36, 56.82, 54.27, 52.60, 46.33, 43.50, 40.42, 37.05, 35.42, 35.26, 34.29, 33.16, 29.65, 26.44, 20.26, 18.35; MS (+EI) m/z (%): 43 (36), 57 (31), 338 (100), 352 (34), 370 (64), 394 (15), 409 (7), 427 (4); HRMS calcd for C$_{26}$H$_{37}$NO$_4$ 427.2723, found 427.27217.

Example 11

Double Deprotection of 1-[(5α,7α)-3-methoxy-4,5-epoxy-18,19-dihydro-7-[(1S)-1-hydroxy-1,2,2-trimethylpropyl]-6-methoxy-6,14-ethenomorphinan-17-yl]-ethanone

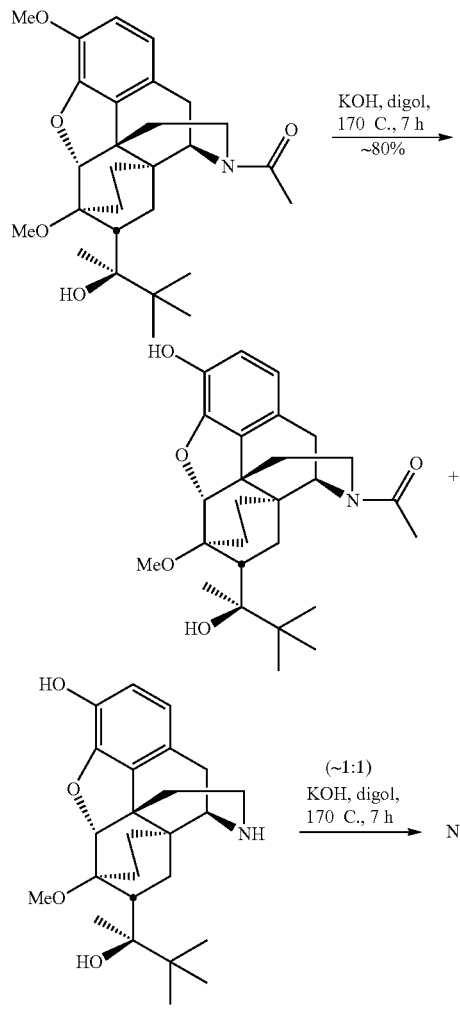

A mixture of 1-[(5α,7α)-3-methoxy-4,5-epoxy-18,19-dihydro-7-[(1S)-1-hydroxy-1,2,2-trimethylpropyl]-6-methoxy-6,14-ethenomorphinan-17-yl]-ethanone (Example 2, 0.1 g; 0.213 mmol), KOH (0.71 g) and digol (2.4 mL) was stirred under inert atmosphere at 170-180° C. for 7 h. The reaction mixture was then quenched with water (10 mL) and the products were extracted with dichloromethane (2×5 mL). Saturated solution of $NH_4Cl$ (1.5 mL) was added to the aqueous layer, which was extracted with dichloromethane (2×5 mL). The addition of saturated solution of $NH_4Cl$ followed by extraction was repeated twice, the pH of water layer was strongly basic, and the mixture turned into a suspension. TLC analysis of the aqueous layer indicated that no product remained. The combined organic layers were washed with water, brine, dried over $Na_2SO_4$ and concentrated. The products were isolated by column chromatography (eluent EtOAc→dichloromethane+20% MeOH).

Product 1: [5α,7α]-17-acetyl-α-(1,1-dimethylethyl)-4,5-epoxy-18,19-dihydro-6-methoxy-α-methyl-6,14-ethenomorphinan-7-methanol, Amide. mp>240° C. (MeOH); $R_f$ 0.45 (ethyl acetate); IR ($CHCl_3$) v 3583, 3390, 3000, 2981, 2876, 1626, 1504, 1457, 1370, 1310, 1159, 1090 cm$^{-1}$; ratio of isomers 1:1.5;

Major isomer: $^1$H NMR (600 MHz, $CDCl_3$) δ 6.77 (d, J=8.1 Hz, 1H), 6.57 (d, J=8.1 Hz, 1H), 5.81 (s, 1H, OH), 4.87 (d, J=7.1 Hz, 1H), 4.46 (s, 1H), 3.65 (dd, J=14.2, 5.5 Hz, 1H), 3.55 (s, 3H), 3.36 (ddd, J=13.5, 13.5, 3.8 Hz, 1H), 2.88 (m, 1H), 2.74 (d, J=18.6 Hz, 1H), 2.17 (s, 3H), 2.09 (m, 1H), 1.99 (m, 1H), 1.94-1.75 (m, 5H), 1.54 (dd, J=13.1, 9.2 Hz, 1H), 1.34 (s, 3H), 1.25-1.19 (m, 1H), 0.99 (s, 9H), 0.76-0.69 (m, 1H); $^{13}$C NMR (150 MHz, $CDCl_3$) δ 168.98, 145.69, 138.03, 131.09, 126.17, 120.22, 117.30, 96.55, 80.44, 79.36, 52.68, 49.70, 46.41, 43.78, 40.29, 38.81, 35.52, 34.91, 32.59, 32.11, 28.56, 26.42, 21.55, 20.10, 17.80;

Minor isomer: $^1$H NMR (600 MHz, $CDCl_3$) δ 6.78 (d, J=8.1 Hz, 1H), 6.57 (d, J=8.1 Hz, 1H), 5.81 (s, 1H, OH), 4.57 (dd, J=13.9, 5.6 Hz, 1H), 4.46 (s, 1H), 3.85 (d, J=6.8 Hz, 1H), 3.56 (s, 3H), 3.00-2.88 (m, 2H), 2.81 (ddd, J=13.4, 13.4, 4.0 Hz, 1H), 2.15 (m, 2H), 2.13 (s, 3H), 1.94-1.75 (m, 5H), 1.44 (m, 1H), 1.36 (s, 3H), 1.19-1.14 (m, 1H), 0.99 (s, 9H), 0.81-0.76 (m, 1H); $^{13}$C NMR (150 MHz, $CDCl_3$) δ 168.92, 145.69, 138.16, 131.13, 125.41, 120.09, 117.38, 96.31, 80.27, 79.28, 56.11, 52.71, 46.27, 43.33, 40.41, 36.08, 33.90, 33.56, 32.83, 32.69, 29.03, 26.39, 21.69, 20.09, 18.01; MS (+EI) m/z (%): 43 (100), 57 (48), 84 (82), 366 (68), 380 (78), 398 (51), 423 (6), 455 (3); HRMS calcd for $C_{27}H_{37}NO_5$ 455.2672, found 455.26633.

Product 2: Norbuprenorphine. mp 227-230° C. (EtOH); $R_f$ 0.24 (DCM+20% methanol); $[α]^{20}_D$=−80.12 (c=1.0, MeOH); IR ($CHCl_3$) v 3587, 3397, 2957, 2848, 1598, 1460, 1124 cm$^{-1}$; $^1$H NMR (600 MHz, $CDCl_3$) δ 6.79 (d, J=8.1 Hz, 1H), 6.59 (d, J=8.1 Hz, 1H), 5.75 (s, 1H, OH), 4.49 (s, 1H), 3.55 (s, 3H), 3.52 (m, 1H), 3.33 (m, 1H), 3.21 (m, 1H), 3.07 (m, 1H), 2.93 (dd, J=18.8, 6.3 Hz, 1H), 2.85 (m, 1H), 2.26-2.10 (m, 2H), 1.97-1.78 (m, 2H), 1.55 (m, 1H), 1.37 (s, 3H), 1.27 (m, 1H), 1.18 (m, 1H), 1.09 (s, 9H), 0.88 (m, 1H), 0.76 (m, 1H); $^{13}$C NMR (150 MHz, DMSO) δ 146.20, 139.65, 130.99, 124.14, 120.19, 118.07, 93.80, 80.15, 79.14, 53.01, 52.49, 44.80, 41.85, 35.70, 34.21, 31.70, 31.58, 29.63, 28.70, 26.74, 20.52, 18.69; MS (+EI) m/z (%): 43 (70), 57 (60), 324 (100), 338 (75), 356 (45), 381 (22), 395 (13), 413 (6); HRMS calcd for $C_{25}H_{35}NO_4$ 413.2566, found 413.25719.

Example 12

5α,7α(R)]-17-(cyclopropylcarbonyl)-α-(1,1-dimethylethyl)-4,5-epoxy-18,19-dihydro-3,6-dimethoxy-6,14-ethenomorphinan-7-methanol

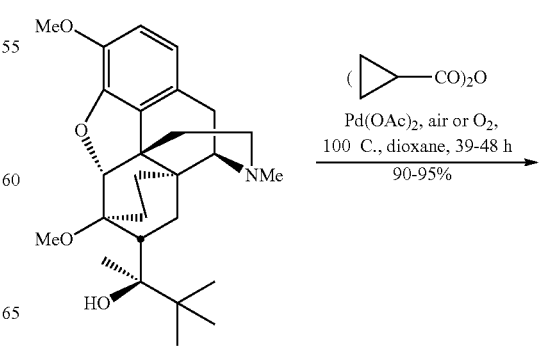

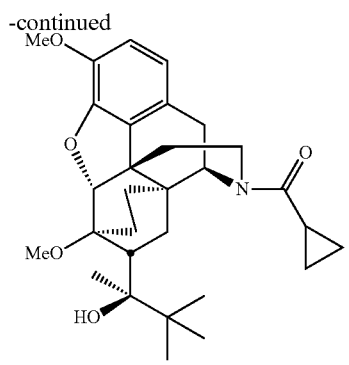

A mixture of [5α,7α]-(1,1-dimethylethyl)-4,5-epoxy-18,19-dihydro-3,6-dimethoxy-α,17-dimethyl-6,14-ethenomorphinan-7-methanol (Example, 1, 0.088 g; 0.2 mmol), Pd(OAc)$_2$ (0.0022 g; 0.01 mmol), Cu(OAc)$_2$ (0.002 g; 0.01 mmol), cyclopropylcarboxylic acid anhydride (0.21 g; 1.4 mmol) and dioxane (1 mL) was stirred under oxygen atmosphere at 100° C. for 39 h. Then the mixture was evaporated to a thick oil and diluted with dichloromethane (10 mL). The resulting mixture was washed with saturated solution of NaHCO$_3$ (10 mL) and after separation the aqueous layer was extracted with dichloromethane (3×5 mL). Combined organic layers were washed with water, brine, dried over Na$_2$SO$_4$ and concentrated. Column chromatography (eluent EtOAc:hexane/1:1) afforded 0.098 g (95%) of the titled compound; ratio of isomers 1:1.5; mp 103-105° C. (MeOH, mixture of isomers); R$_f$ 0.70 (ethyl acetate); IR (CHCl$_3$) ν 3397, 3002, 2957, 2841, 1628, 1503, 1453, 1440, 1162, 944 cm$^{-1}$;

Major isomer: $^1$H NMR (600 MHz, CDCl$_3$) 6.76 (d, J=8.1 Hz, 1H), 6.62 (d, J=8.1 Hz, 1H), 5.77 (s, 1H), 4.85 (d, J=7.1 Hz, 1H), 4.44 (s, 1H), 4.06 (dd, J=14.1, 5.0 Hz, 1H), 3.89 (s, 3H), 3.55 (s, 3H), 3.38 (ddd, J=13.7, 13.7, 3.6 Hz, 1H), 2.91 (m, 1H), 2.77 (d, J=18.6, 1H), 2.06 (dd, J=9.8, 9.8 Hz, 1H), 1.92-1.70 (m, 4H), 1.47 (d, J=12.6, 1H), 1.32 (s, 3H), 1.20 (m, 1H), 1.10 (m, 1H), 0.97 (s, 9H), 0.86 (m, 1H), 0.73-0.83 (m, 2H), 0.70 (m, 1H); $^{13}$C NMR (150 MHz, CDCl$_3$) δ 171.75, 147.05, 142.68, 131.53, 127.10, 119.85, 114.60, 96.48, 80.40, 79.14, 56.79, 52.69, 50.13, 46.45, 44.07, 40.25, 37.81, 35.82, 35.38, 32.61, 31.85, 28.68, 26.36, 19.95, 17.79, 11.08, 7.87, 6.64;

Minor isomer: $^1$H NMR (600 MHz, CDCl$_3$) 6.77 (d, J=8.1 Hz, 1H), 6.62 (d, J=8.1 Hz, 1H), 5.80 (s, 1H), 4.54 (dd, J=14.0, 5.3 Hz, 1H), 4.44 (s, 1H), 4.29 (d, J=6.6 Hz, 1H), 3.89 (s, 3H), 3.55 (s, 3H), 3.02 (dd, J=18.5, 6.8 Hz, 1H), 2.94 (m, 1H), 2.84 (ddd, J=13.6, 13.6, 3.9 Hz, 1H), 2.19 (ddd, J=11.8, 11.8, 3.7 Hz, 1H), 2.13 (dd, J=9.7, 9.6 Hz, 1H) 1.92-1.70 (m, 5H), 1.46 (d, J=12.6, 1H), 1.35 (s, 3H), 1.18 (m, 1H), 1.07-0.98 (m, 2H), 0.98 (s, 9H), 0.73-0.83 (m, 3H); $^{13}$C NMR (150 MHz, CDCl$_3$) δ 171.75, 147.00, 142.20, 131.62, 126.47, 119.71, 114.71, 96.14, 80.26, 79.14, 56.85, 54.99, 52.69, 46.24, 43.35, 40.35, 36.20, 34.09, 34.08, 33.00, 32.76, 29.17, 26.32, 20.12, 18.07, 11.14, 7.72, 7.42;

MS (+EI) m/z (%): 41 (68), 56 (55), 69 (100), 86 (89), 124 (19), 167 (15), 406 (29), 438 (25), 495 (1); HRMS calcd for C$_{30}$H$_{41}$NO$_5$ 495.2985, found 495.29906.

Example 13

[5α,7α(S)]-17-(cyclopropylmethyl)-α-(1,1-dimethylethyl)-4,5-epoxy-18,19-dihydro-3,6-dimethoxy-α-methyl-, [5α,7α(S)]-6,14-ethenomorphinan-7-methanol Method A:

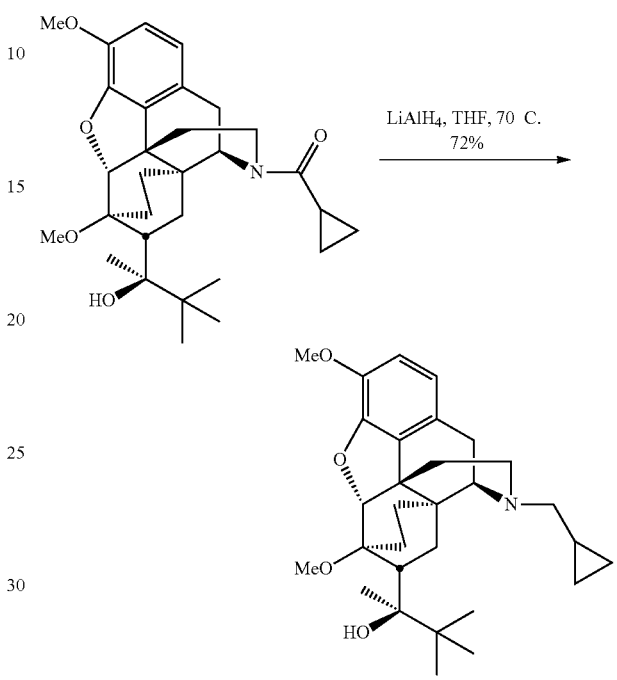

To the solution of 5α,7α(R)]-17-(cyclopropylcarbonyl)-α-(1,1-dimethylethyl)-4,5-epoxy-18,19-dihydro-3,6-dimethoxy-6,14-ethenomorphinan-7-methanol (Example 5, 0.11 g; 0.22 mmol) in THF (2 mL) was added LiAlH$_4$ (0.012 g; 0.33 mmol) in one portion at room temperature. After 5 min the resulting reaction mixture was placed into an oil bath and stirred at reflux for 90 min. The mixture was allowed to cool and then quenched with EtOAc (1 mL). The mixture was stirred for 15 min, then water was added (0.015 g), followed by the addition of 15% ww solution of NaOH (0.015 g), and, finally, the addition of water (0.043 g) [Fieser's workup]. The resulting suspension was stirred for 30 min, organic supernatant was decanted, and the precipitate was vigorously stirred in EtOAc (10 mL). This operation was repeated four-times, the combined EtOAC extracts were evaporated to dryness, and the residue was subjected to column chromatography (eluent EtOAc:hexane/1:1) to afford 0.08 g (72%) of the titled compound as a white solid;

Method B:

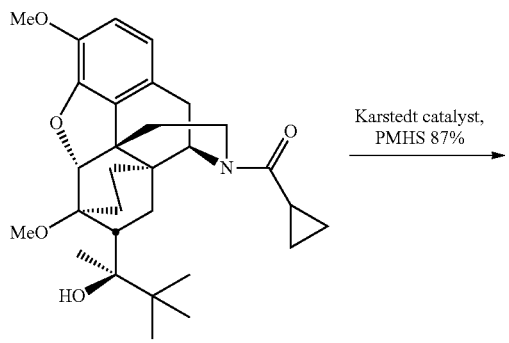

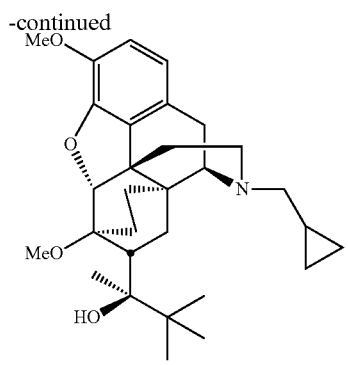

The flame dried flask thoroughly purged with Argon was charged with 5α,7α(R)]-17-(cyclopropylcarbonyl)-α-(1,1-dimethylethyl)-4,5-epoxy-18,19-dihydro-3,6-dimethoxy-6,14-ethenomorphinan-7-methanol (Example 5, 0.135 g; 0.272 mmol), toluene (3 mL), PMHS (0.098 g; 1.63 mmol of Si—H bond) and the Karstedt's catalyst (0.80 g of approx. 2% w/w Pt solution in xylene) was added dropwise. After 5 min gentle bubbling deceased and the color of reaction mixture turned to yellow. The mixture was slowly stirred for 3 h, then methanol (4 mL) and NaOH (0.14 g) were added. The mixture was stirred at 80° C. for 2 h, then concentrated under vacuum, and diluted with water and EtOAc. The mixture was extracted three times with EtOAc and the combined organic layers were washed with water, brine, dried over $Na_2SO_4$ and concentrated. Column chromatography (eluent EtOAc:hexane/1:3) afforded 0.115 g (87%) of the titled compound.

Method C:

pre-heated oil bath at 85° C. and stirred for 18 h. After this time it was diluted with water (20 mL), extracted three times with EtOAc and the combined organic layers were washed with water (2×10 mL), brine, dried over $Na_2SO_4$ and concentrated. Column chromatography (eluent EtOAc:hexane/1:1) afforded 0.13 g (88%) of the titled compound. mp 65-68° C. (EtOH); $R_f$ 0.65 (ethyl acetate:hexane/1:1); $[α]^{20}_D$=−107.51 (c=1.0, $CHCl_3$); IR ($CHCl_3$) v 3389, 2981, 2958, 2839, 1630, 1502, 1454, 1129, 1057, 942 $cm^{-1}$; $^1H$ NMR (600 MHz, $CDCl_3$) δ 6.70 (d, J=8.0 Hz, 1H), 6.65 (d, J=8.0 Hz, 1H), 5.92 (s, 1H, OH), 4.44 (s, 1H), 3.88 (s, 3H), 3.55 (s, 3H), 3.00 (d, J=9.4 Hz, 1H), 2.98 (m, 1H), 2.90 (ddd, J=11.9, 11.9, 3.4 Hz, 1H), 2.60 (dd, J=11.9, 5.1 Hz, 1H), 2.36 (dd, J=12.5, 5.9 Hz, 1H), 2.30 (m, 2H), 2.24 (dd, J=18.3, 6.5 Hz, 1H), 2.16 (dd, J=9.9, 9.8 Hz, 1H), 1.98 (ddd, J=12.7, 12.7, 5.6 Hz, 1H), 1.88-1.75 (m, 2H), 1.68 (dd, J=12.7, 2.2 Hz, 1H), 1.37 (s, 3H), 1.31 (dd, J=12.9, 9.5 Hz, 1H), 1.08 (m, 1H), 1.05 (s, 9H), 0.81 (m, 1H), 0.72 (m, 1H), 0.54-0.45 (m, 2H), 0.12 (m, 2H); $^{13}C$ NMR (150 MHz, $CDCl_3$) δ 146.87, 141.64, 132.89, 128.92, 119.14, 113.97, 96.73, 80.76, 79.35, 59.53, 58.26, 56.82, 52.60, 46.19, 43.91, 43.69, 40.38, 35.92, 35.77, 33.44, 29.74, 26.44, 22.84, 20.08, 18.17, 9.53, 4.19, 3.25; MS (+EI) m/z (%): 43 (53), 84 (82), 108 (47), 253 (11), 366 (9), 392 (100), 424 (29), 448 (9), 481 (11); HRMS calcd for $C_{30}H_{43}NO_4$ 481.3192, found 481.31995.

Example 14

Buprenorphine

Method A

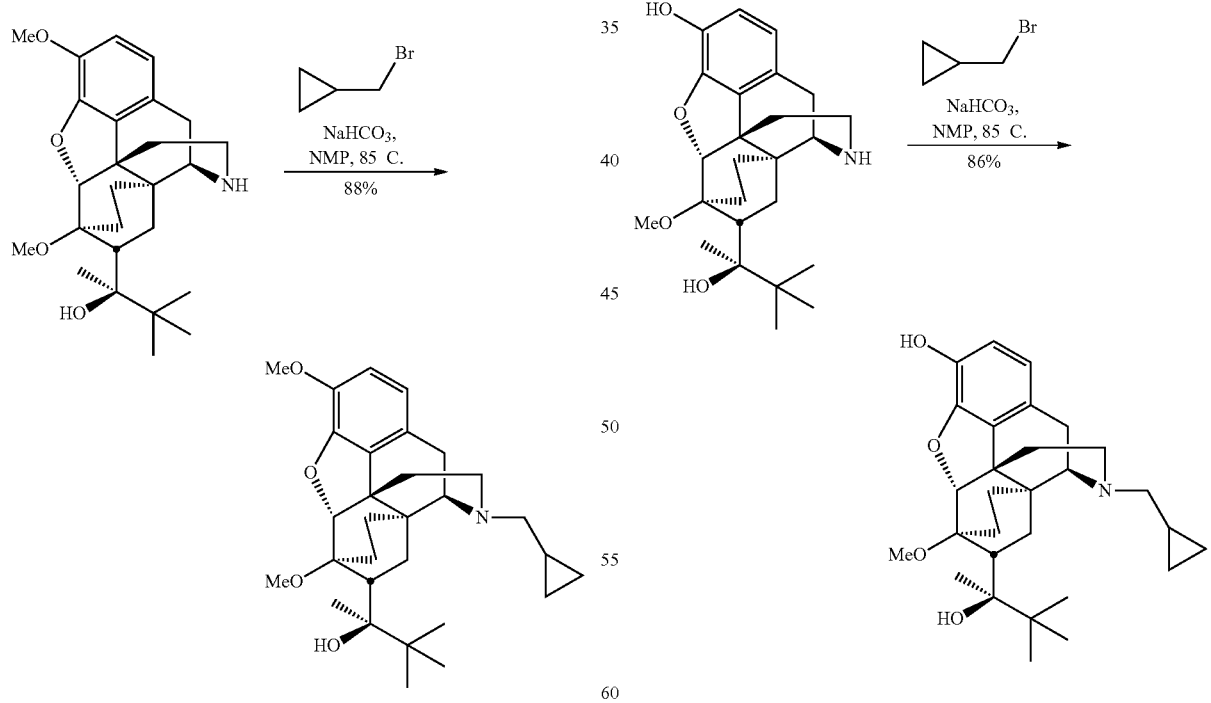

To the solution of [5α,7α]-α-(1,1-dimethylethyl)-4,5-epoxy-18,19-dihydro-3,6-dimethoxy-α-methyl-6,14-ethenomorphinan-7-methanol (Example 3, 0.13 g; 0.304 mmol) in N-methylpyrrolidine (2 mL) was added $NaHCO_3$ (0.03 g; 0.365 mmol) and finally cyclopropylmethyl bromide (0.061 g; 0.456 mmol). The reaction mixture was placed into a To the solution of norbuprenorphine (Example 4, 0.07 g; 0.169 mmol) in N-methylpyrrolidine (1 mL) was added $NaHCO_3$ (0.017 g; 0.203 mmol) and cyclopropylmethyl bromide (0.034 g; 0.253 mmol). The reaction mixture was placed into a pre-heated oil bath at 80° C. and stirred over 18 h. It was then diluted with water (10 mL), extracted three times with EtOAc, and the combined organic layers were washed with water (2×5 mL), brine, dried over Na₂SO₄ and concentrated. Column chromatography (eluent EtOAc:hexane/1:2) afforded 0.068 g (86%) of buprenorphine.
Method B

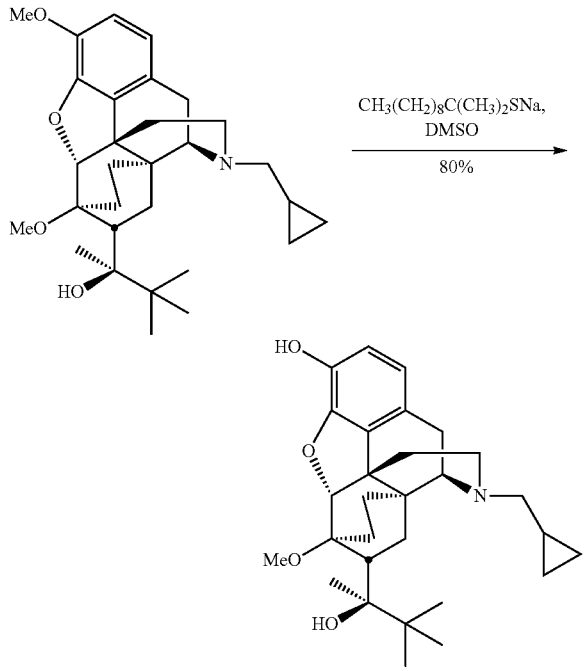

To DMSO (1.1 mL) thoroughly purged with nitrogen was added freshly prepared NaOEt (0.097 g; 1.43 mmol) and dodecanethiol (0.29 g; 1.43 mmol). A suspension formed and was again purged with nitrogen. After 5 min the reaction mixture was placed into an oil bath pre-heated to 145° C. When the solid dissolved, indicating that the thiolate formation was complete, a solution of [5α,7α(S)]-17-(cyclopropylmethyl)-α-(1,1-dimethylethyl)-4,5-epoxy-18,19-dihydro-3,6-dimethoxy-α-methyl-, [5α,7α(S)]-6,14-ethenomorphinan-7-methanol (Example 6, 0.23 g; 0.477 mmol) in DMSO (1.1 mL) was added over 2 min. After 2 h the reaction mixture was allowed to cool down, diluted with water (10 mL), and the pH was adjusted to approx 2 by addition of 6M HCl. This mixture was washed twice with hexane (2×2 mL) and finally the pH of the aqueous layer was adjusted to approximately 8. A white precipitate formed and the mixture was extracted with EtOAc, the pH was again adjusted to approximately 8-9, and the product was extracted with EtOAc. The operation involving the pH adjustment and subsequent extraction was repeated once more. Combined organic layers were washed with water (2×5 mL), brine, dried over Na₂SO₄ and concentrated. Column chromatography (eluent EtOAc:hexane/1:2) afforded 0.18 g (80%) of buprenorphine (1); mp 217-218° C. (MeOH); R$_f$ 0.23 (EtOAc:hexane/1:2); [α]$^{20}$$_D$=−104.17 (c=1, CHCl₃); IR (CHCl₃) ν 3583, 3389, 2982, 2952, 2815, 1633, 1503, 1370, 1132; ¹H NMR (600 MHz, CDCl₃) δ 6.69 (d, J=8.0 Hz, 1H), 6.50 (d, J=8.0 Hz, 1H), 6.01 (s, 1H), 5.46 (bs, 1H), 4.47 (d, J=1.2 Hz, 1H), 3.54 (s, 3H), 3.00 (bs, 1H), 2.99 (d, J=13.4 Hz, 1H), 2.90 (m, 1H), 2.62 (dd, J=11.9, 5.1 Hz, 1H), 2.37 (dd, J=12.6, 6.0 Hz, 1H), 2.40-2.27 (m, 2H), 2.23 (dd, J=18.3, 6.5 Hz, 1H), 2.17 (dd, J=9.8, 9.8 Hz, 1H), 1.99 (ddd, J=12.6, 12.6, 5.6 Hz, 1H), 1.85 (m, 1H), 1.77 (m, 1H), 1.69 (dd, J=12.8, 2.5 Hz, 1H), 1.38 (s, 3H), 1.32 (dd, J=18.9, 9.2 Hz, 1H), 1.08 (m, 1H), 1.05 (s, 9H), 0.81 (m, 1H), 0.72 (m, 1H), 0.52-0.45 (m, 2H), 0.13 (m, 2H); ¹³C NMR (150 MHz, CDCl₃) δ 145.48, 137.32, 132.59, 128.29, 119.57, 116.44, 96.98, 80.86, 79.69, 59.53, 58.26, 52.57, 46.47, 43.72, 43.65, 40.39, 35.98, 35.65, 33.42, 29.63, 26.43, 22.88, 20.13, 18.21, 9.49, 4.20, 3.26; MS (+EI) m/z (%): 55 (100), 71 (64), 149 (26), 366 (21), 378 (92), 410 (31), 435 (20), 449 (23), 467 (25); HRMS calcd for C₂₉H₄₁NO₄ 467.3036, found 467.30431.

Example 15

Cyclopropanecarboxylic Acid Anhydride

To a solution of cyclopropylcarboxylic acid (15.15 g; 0.176 mol), DCM (200 mL) and hexane (100 mL) was added triethylamine (18.69 g; 0.184 mol) dropwise while the flask was placed into an ice bath. After one hour cyclopropylcarboxylic acid chloride (18.4 g; 0.176 mol) was added dropwise over 10 min. The addition resulted in a thick suspension of triethylammonium hydrochloride. The mixture was vigorously stirred at room temperature for 2 h and then the precipitate was filtered off. The filtration cake was washed with hexane and the combined filtrates were concentrated under reduced pressure to approximately 50 mL volume. Any additional precipitate was again filtered off and the cake was washed with hexane. The solvent was removed under reduced pressure and the residue was distilled under high vacuum. The product was collected in two fractions (4.19 g (65-72° C./0.7 Torr) and 19.35 g (72-73° C./0.7 Torr) in 86% overall yield.

Example 16

[5α,7α(S)]-17-(Cyclopropylcarbony)-α-(1,1-dimethylethyl)-4,5-epoxy-3-[(ethoxycarbonyl)oxy]-18,19-dihydro-6-methoxy-α-methyl-6,14-ethenomorphinan-7-methanol

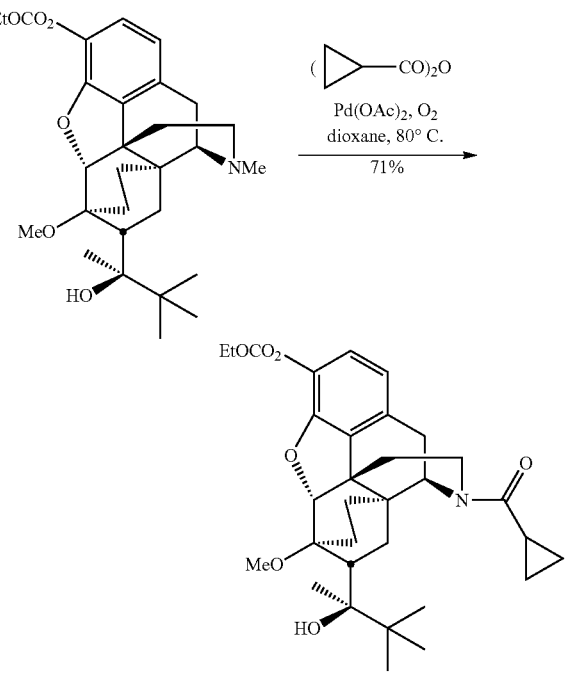

[(5α,7α(S)]-α-(1,1-Dimethylethyl)-4,5-epoxy-3-[(ethoxycarbonyl)oxy]-18,19-dihydro-6-methoxy-α,17-dimethyl-6,14-ethanomorphinan-7-methanol (900 mg, 1.80 mmol), cyclopropyl carboxylic acid anhydride (2.70 g, 18.00 mmol), Pd(OAc)$_2$ (19.8 mg, 0.09 mmol), and Cu(OAc)$_2$ (18.0 mg, 0.09 mmol) were suspended in dioxane (18 mL). The mixture was three times evacuated/refilled with O$_2$ gas. Then it was subjected to an atmosphere of O$_2$ gas while stirring at 80° C. for 12 h. TLC analysis indicated disappearance of starting material (silica gel, DCM/MeOH; 10:1). The solvent was removed using rotary evaporation and the residue was chromatographed on silica gel using EtOAc/hexanes (4:1) as eluent to afford the titled compound as a yellow solid (800 mg, 80% yield).

m.p. 238-239° C. (EtOAc/hex); $[\alpha]_D^{20}$=−58.34° (c=0.5, DCM); R$_f$ 0.67 (10:1; DCM/MeOH); IR (cm$^{-1}$) IR (CHCl$_3$) ν 3436, 2979, 1762, 1634, 1450, 1369, 1207, 1162, 1078, 734 cm$^{-1}$; $^1$H NMR (300 MHz, CDCl$_3$) δ 6.96 (d, 1H, J=8.1 Hz), 6.68 (d, 1H, J=8.1 Hz), 5.80 (d, 1H, 13.2 Hz), 4.49 (s, 1H), 4.29 (q, 2H, J=7.2 Hz), 3.51 (s, 3H), 2.79-3.04 (m, 2H), 1.74-2.06 (m, 8H), 1.45-1.55 (m, 1H), 1.37 (s, 3H), 1.37 (t, 3H, J=7.2 Hz), 1.31-1.39 (m, 1H), 1.06-1.29 (m, 2H), 0.95-1.05 (m, 1H), 1.05 (s, 9H), 0.68-0.90 (m, 5H); $^{13}$C NMR (125 MHz, CDCl$_3$) δ; MS (FAB+) m/z (%) 554(30), 536(15), 496(15), 83(20), 69(100), 55(50), 41(75); HRMS (FAB+) calcd for C$_{29}$H$_{42}$NO$_6$ 554.32260, found 554.31178.

Example 17

Buprenorphine

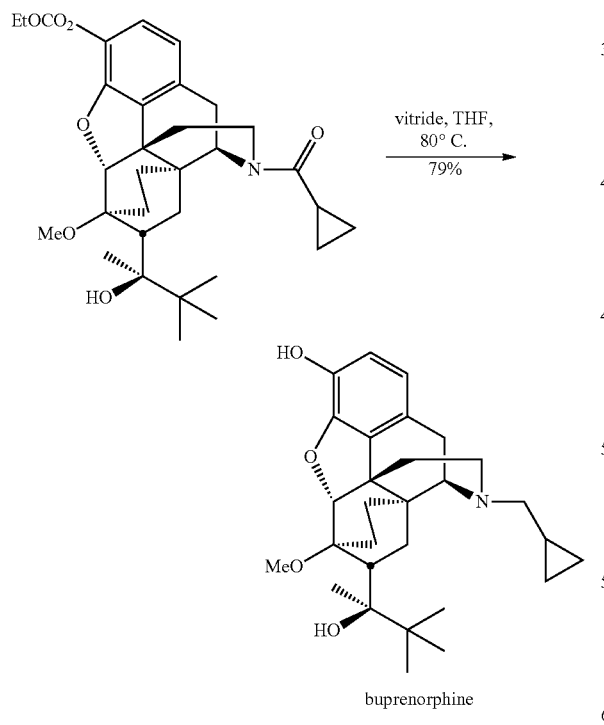

buprenorphine

[5α,7α(S)]-17-(Cyclopropylcarbony)-α-(1,1-dimethyl-ethyl)-4,5-epoxy-3-[(ethoxycarbonyl)oxy]-18,19-dihydro-6-methoxy-α-methyl-6,14-ethenomorphinan-7-methanol (Example 14, 30 mg, 0.05 mmol) in THF (0.5 mL) was added to Vitride (0.50 mL, 10% wt in toluene) at room temperature. A vigorous bubbling was observed. The resulting mixture was heated to 80 C for 30 min. To the reaction mixture cooled down to room temperature was added Rochelle's salt (1 mL). The resulting suspension was extracted with Et$_2$O (3×5 mL). The combined extracts were dried over Na$_2$SO$_4$, filtered and concentrated using rotary evaporation. The residue was purified by flash column chromatography on silica gel using hexanes/EtOAc (1:1) as eluent to afford buprenorphine 1 as a white solid (20 mg, 79% yield).

One or more currently preferred embodiments have been described by way of example. It will be apparent to persons skilled in the art that a number of variations and modifications can be made without departing from the scope of the invention as defined in the claims.

What is claimed is:
1. A method of preparing a compound of Formula I:

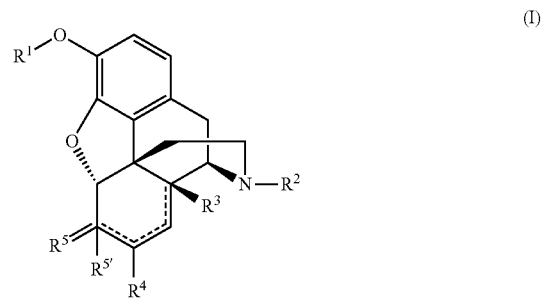

comprising reacting a compound of Formula II:

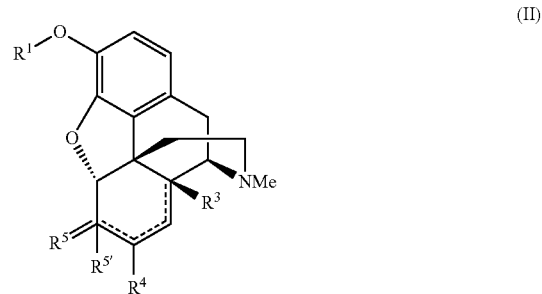

in the presence of a metal catalyst, wherein the catalyst comprises Cu, Ru, Rh, Ir, Pt, Os, Ag, Au and/or Pd, and a compound of Formula III:

$$R^2\text{-LG} \quad (III),$$

or when R$^2$ is C(O)R$^6$, a compound of Formula IV:

$$R^6\text{=C=O} \quad (IV)$$

wherein,
R$^1$ is selected from H, C$_{1-10}$alkyl, C(O)C$_{1-10}$alkyl, C(O)OC$_{1-10}$alkyl and PG$^1$;
R$^2$ is selected from C(O)R$^6$, C(O)OR$^6$, S(O)R$^6$, SO$_2$R$^6$, P(O)R$^6$R$^{6'}$, P(O)(OR$^6$)R$^{6'}$, P(O)(OR$^6$)(OR$^{6'}$), C(O)NR$^6$R$^{6'}$ and C(O)SR$^6$;
R$^3$ is selected from H, OH, OC$_{1-10}$alkyl, OC(O)C$_{1-10}$alkyl, OC(O)OC$_{1-10}$alkyl and OPG$^2$ or R$^3$ is not present when the carbon atom to which it is attached is sp$^2$ hybridized;
R$^4$ is selected from H, C$_{1-10}$alkyl, C(O)C$_{1-10}$alkyl, hydroxyl-substituted C$_{1-10}$alkyl, and PG$^3$-O-substituted C$_{1-10}$alkyl;
R$^5$ is selected from OH, OC$_{1-10}$alkyl, OC(O)C$_{1-10}$alkyl, OC(O)OC$_{1-10}$alkyl and OPG$^4$ when the ═ to which it is attached is a single bond, or $R^5$ is O when the ⹀ to which it is attached is a double bond, $R^{5'}$ is not present when $R^5$ ⹀ is $R^{5=}$ or $R^{5'}$ is H when $R^5$ ⹀ is $R^{5-}$ and the carbon to which it is attached is sp$^3$ hybridized;

$R^6$ and $R^{6'}$ are independently selected from $C_{3-10}$cycloalkyl, $C_{3-10}$heterocycloalkyl, $C_{3-10}$cycloalkenyl, $C_{1-20}$alkyl, $C_{2-20}$alkenyl, $C_{2-20}$alkynyl, $C_{6-10}$aryl and $C_{5-10}$heteroaryl, each of the latter eight groups being unsubstituted or substituted with one or more substituents independently selected from $R^7$, $OR^8$, $SiR^7R^7R^8$, $NR^8R^{8'}$, $SR^8$, $S(O)R^7$, $SO_2R^7$, halo, CN and $NO_2$;

$R^7$ and $R^{7'}$ are independently selected from $C_{1-6}$alkyl, $C_{6-10}$aryl and $C_{1-6}$alkylene$C_{6-10}$aryl;

$R^8$ and $R^{8'}$ are independently selected from H, PG$^5$, $C_{1-6}$alkyl, $C_{6-10}$aryl and $C_{1-6}$alkylene$C_{6-10}$aryl;

⹀ represents a single or double bond, provided that two double bonds are not adjacent to each other;

PG$^1$, PG$^2$, PG$^3$, PG$^4$ and PG$^5$ are independently, a protecting group that is removable after the preparation of the compound of Formula I; and LG is a leaving group, wherein, when (a) $R^1$, $R^8$ and/or $R^{8'}$ are H; (b) $R^3$ and/or $R^5$ is OH; and/or (c) $R^4$ is hydroxyl-substituted $C_{1-10}$alkyl, the method further comprises removal of any $R^2$ group in $R^1$, $R^8$, $R^{8'}$, $R^3$, $R^5$ and/or $R^4$.

2. The method of claim 1 further comprising reacting the compound of Formula II with the compound of Formula III or IV, in the presence of the metal catalyst and an oxidant.

3. The method of claim 2, wherein the oxidant is $O_2$, air and/or an organic or inorganic peroxide.

4. The method of claim 1, wherein $R^1$ is selected from H, $C_{1-6}$alkyl, $C(O)C_{1-6}$alkyl, $C(O)OC_{1-6}$alkyl and PG$^1$.

5. The method of claim 4, wherein $R^1$ is selected from H, PG$^1$, Me, Et, C(O)Me, C(O)Et, C(O)OMe and C(O)OEt.

6. The method of claim 1, wherein $R^2$ is selected from $C(O)R^6$, $C(O)OR^6$, and $C(O)NR^6R^{6'}$.

7. The method of claim 6, wherein $R^2$ is $C(O)R^6$.

8. The method of claim 1, wherein $R^6$ and $R^{6'}$ are independently selected from $C_{3-7}$cycloalkyl, $C_{3-7}$heterocycloalkyl, $C_{3-7}$cycloalkenyl, $C_{1-15}$alkyl, $C_{2-15}$alkenyl, $C_{2-15}$alkynyl, $C_{6-10}$aryl and $C_{5-10}$heteroaryl, each of the latter eight groups being unsubstituted or substituted with one, two, three or four substituents independently selected from $R^7$, $OR^8$, halo, CN and $NO_2$.

9. The method of claim 8, wherein $R^6$ and $R^{6'}$ are independently selected from cyclopropyl, cyclobutyl, cyclopentyl, cyclohexyl, Me, Et, i-Pr, Pr, n-Bu, s-Bu, t-Bu, n-pentyl, n-hexyl, n-heptyl, n-octyl, n-nonyl, n-decyl, n-undecyl, allyl, propargyl and phenyl, each of the these groups being unsubstituted.

10. The method of claim 1, wherein $R^3$ is selected from H, OH, $OC_{1-6}$alkyl, $OC(O)C_{1-6}$alkyl, $OC(O)OC_{1-6}$alkyl and OPG$^2$ or $R^3$ is not present when the carbon atom to which it is attached is sp$^2$ hybridized.

11. The method of claim 10, wherein $R^3$ is selected from H, OH, OMe, OEt, OC(O)Me, OC(O)Et, OC(O)OMe, OC(O)OEt and OPG$^2$ or $R^3$ is not present when the carbon atom to which it is attached is sp$^2$ hybridized.

12. The method of claim 11, wherein $R^3$ is selected from H, OPG$^2$ and OH or $R^3$ is not present when the carbon atom to which it is attached is sp$^2$ hybridized.

13. The method of claim 1, wherein $R^4$ is selected from H, $C(O)C_{1-6}$alkyl, hydroxyl-substituted $C_{1-10}$alkyl, and PG$^3$-O-substituted $C_{1-10}$alkyl.

14. The method of claim 13, wherein $R^4$ is selected from H, $C(O)C_{1-4}$-alkyl and hydroxyl-substituted $C_{2-8}$alkyl.

15. The method of claim 14, wherein $R^4$ is selected from H, C(O)Me and C(Me)(OH)(t-butyl).

16. The method of claim 1, wherein the ⹀ to which $R^5$ is attached is a single bond and $R^5$ is selected from OH, OPG$^4$, $OC_{1-6}$alkyl, $OC(O)C_{1-6}$alkyl, $OC(O)OC_{1-6}$alkyl and OPG$^4$.

17. The method of claim 16, wherein the ⹀ to which $R^5$ is attached is a single bond and $R^5$ is selected from OH, OPG$^4$, OMe, OEt, OC(O)Me, OC(O)Et, OC(O)OMe, OC(O)OEt and OPG$^4$.

18. The method of claim 17, wherein the ⹀ to which $R^5$ is attached is a single bond and $R^5$ is selected from OH, OPG$^4$ and OMe.

19. The method of claim 1, wherein the ⹀ to which $R^5$ is attached is a double bond and $R^5$ is O.

20. The method of claim 1, wherein $R^7$ and $R^{7'}$ are independently selected from Me, Et, Ph and Bn.

21. The method of claim 1, wherein $R^8$ and $R^{8'}$ are independently selected from H, PG$^5$, Me, Et, Ph and Bn.

22. The method of claim 1, wherein PG$^1$, PG$^2$, PG$^3$, PG$^4$ and PG$^5$ are independently selected from t-Boc, Ac, Ts, Ms, silyl ethers, Tf, Ns, Bn, Fmoc, benzoyl, dimethoxytrityl, methoxyethoxymethyl ether, methoxymethyl ether, pivaloyl, p-methoxybenzyl ether, tetrahydropyranyl, trityl, ethoxyethyl ethers, carbobenzyloxy and benzoyl.

23. The method of claim 1, wherein LG is selected from Cl, Br, CN, CCl$_3$, imidazole, pentafluorophenyl, acyl, O—$R^2$, NH—$R^2$, S—$R^2$, OTs, ONs and OMs.

24. The method of claim 23, wherein LG is Cl or O—$R^2$.

25. The method of claim 1, wherein, in the compounds of Formula II, the ⹀ bonds, $R^3$, $R^4$ and $R^5$ are selected to provide a compound of Formula II(a):

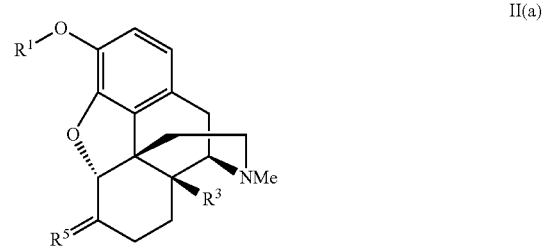

II(a)

wherein $R^1$ is H, $C_{1-10}$alkyl, $C(O)C_{1-10}$alkyl, $C(O)OC_{1-10}$alkyl or PG$^1$; $R^3$ is H, OH, $OC_{1-10}$alkyl, $OC(O)C_{1-10}$alkyl, $OC(O)OC_{1-10}$alkyl or OPG$^2$; and $R^5$ is OH, $OC_{1-10}$alkyl, $OC(O)C_{1-10}$alkyl, $OC(O)OC_{1-10}$alkyl or OPG$^4$, when ⹀ is a single bond and $R^5$ is O when ⹀ is a double bond;

a compound of Formula II(b)

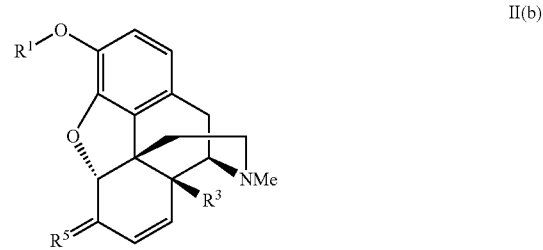

II(b)

wherein $R^1$ is H, $C_{1-10}$alkyl, $C(O)C_{1-10}$alkyl, $C(O)OC_{1-10}$alkyl or PG$^1$; $R^3$ is H, OH, $OC_{1-10}$alkyl, $OC(O)C_{1-10}$alkyl, $OC(O)OC_{1-10}$alkyl or OPG$^2$; and $R^5$ is OH, $OC_{1-10}$alkyl, $OC(O)C_{1-10}$alkyl, $OC(O)OC_{1-10}$alkyl or $OPG^4$, when --- is a single bond and $R^5$ is O when --- is a double bond;

a compound of Formula II(c):

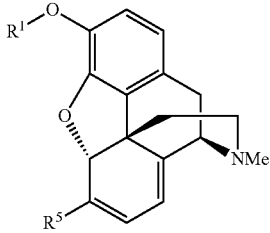

II(c)

wherein $R^1$ is H, $C_{1-10}$alkyl, $C(O)C_{1-10}$alkyl, $C(O)OC_{1-10}$alkyl or $PG^1$; and $R^5$ is OH, $OC_{1-10}$alkyl, $OC(O)C_{1-10}$alkyl, $OC(O)OC_{1-10}$alkyl or $OPG^4$; or a compound of Formula II(d):

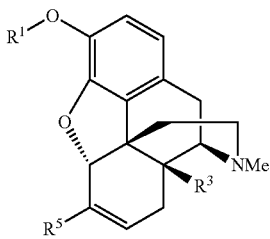

II(d)

wherein $R^1$ is H, $C_{1-10}$alkyl, $C(O)C_{1-10}$alkyl, $C(O)OC_{1-10}$alkyl or $PG^1$; $R^3$ is H, OH, $OC_{1-10}$alkyl, $OC(O)C_{1-10}$alkyl, $OC(O)OC_{1-10}$alkyl or $OPG^2$; and $R^5$ is OH, $OC_{1-10}$alkyl, $OC(O)C_{1-10}$alkyl, $OC(O)OC_{1-10}$alkyl or $OPG^4$.

26. The method of claim 25, wherein $R^1$ is H, Me, $PG^1$ or C(O)Me; $R^3$ is H, $OPG^2$ or OH; $R^4$ is C(Me)(OH)(t-butyl) or C(O)Me; $R^5$ is OH, $OPG^4$ or OMe; and --- is a single bond.

27. The method of claim 1, wherein the compound of Formula II is selected from thebaine, oripavine, 14-hydroxycodeinone, 14-hydroxymorphinone, morphine, codeine, hydromorphone, hydrocodone, oxymorphone, oxycodone, hydromorphol and oxymorphol.

28. The method of claim 1, wherein the compound of Formula III is a compound of Formula III(a):

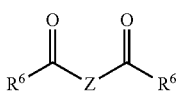

III(a)

wherein
Z is NH, S or O;
$R^6$ is selected from $C_{3-10}$cycloalkyl, $C_{3-10}$heterocycloalkyl, $C_{3-10}$cycloalkenyl, $C_{1-20}$alkyl, $C_{2-20}$alkenyl, $C_{2-20}$alkynyl, $C_{6-10}$aryl and $C_{5-10}$heteroaryl, each of the latter eight groups being unsubstituted or substituted with one or more substituents independently selected from $R^7$, $OR^8$, $SiR^7R^{7'}R^8$, $NR^8R^{8'}$, $SR^8$, $S(O)R^7$, $SO_2R^7$, halo, CN and $NO_2$;
$R^7$ and $R^{7'}$ are independently selected from $C_{1-6}$alkyl, $C_{6-10}$aryl and $C_{1-6}$alkylene$C_{6-10}$aryl; and
$R^8$ and $R^{8'}$ are independently selected from H, $PG^5$, $C_{1-6}$alkyl, $C_{6-10}$aryl and $C_{1-6}$alkylene$C_{6-10}$aryl;

a compound of Formula III(b)

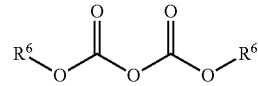

III(b)

wherein
$R^6$ is selected from $C_{3-10}$cycloalkyl, $C_{3-10}$heterocycloalkyl, $C_{3-10}$cycloalkenyl, $C_{1-20}$alkyl, $C_{2-20}$alkenyl, $C_{2-20}$alkynyl, $C_{6-10}$aryl and $C_{5-10}$heteroaryl, each of the latter eight groups being unsubstituted or substituted with one or more substituents independently selected from $R^7$, $OR^8$, $SiR^7R^{7'}R^8$, $NR^8R^{8'}$, $SR^8$, $S(O)R^7$, $SO_2R^7$, halo, CN and $NO_2$;
$R^7$ and $R^{7'}$ are independently selected from $C_{1-6}$alkyl, $C_{6-10}$aryl and $C_{1-6}$alkylene$C_{6-10}$aryl; and
$R^8$ and $R^{8'}$ are independently selected from H, $PG^5$, $C_{1-6}$alkyl, $C_{6-10}$aryl and $C_{1-6}$alkylene$C_{6-10}$aryl;

or a compound of Formula III(c):

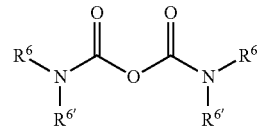

III(c)

$R^6$ and $R^{6'}$ are independently selected from $C_{3-10}$cycloalkyl, $C_{3-10}$heterocycloalkyl, $C_{3-10}$cycloalkenyl, $C_{1-20}$alkyl, $C_{2-20}$ alkenyl, $C_{2-20}$alkynyl, $C_{6-10}$aryl and $C_{5-10}$heteroaryl, each of the latter eight groups being unsubstituted or substituted with one or more substituents independently selected from $R^7$, $OR^8$, $SiR^7R^{7'}R^8$, $NR^8R^{8'}$, $SR^8$, $S(O)R^7$, $SO_2R^7$, halo, CN and $NO_2$;
$R^7$ and $R^{7'}$ are independently selected from $C_{1-6}$alkyl, $C_{6-10}$aryl and $C_{1-6}$alkylene$C_{6-10}$aryl; and
$R^8$ and $R^{8'}$ are independently selected from H, $PG^5$, $C_{1-6}$alkyl, $C_{6-10}$ aryl and $C_{1-6}$alkylene$C_{6-10}$aryl.

29. The method of claim 28, wherein Z is O and $R^6$ and $R^{6'}$ are independently selected from cyclopropyl, cyclobutyl, cyclopentyl, cyclohexyl, Me, Et, i-Pr, Pr, n-Bu, s-Bu, t-Bu, n-pentyl, n-hexyl, n-heptyl, n-octyl, n-nonyl, n-decyl, n-undecyl, allyl, propargyl and phenyl, each of the these groups being unsubstituted.

30. The method of claim 1, wherein the metal catalyst is a Pd(0) or Pd(II) catalyst.

31. The method of claim 30, wherein the metal catalyst is selected from $Pd(OAc)_2$, $PdCl_2$, $PdCl_2(PPh_3)_4$, $PdBr_2$, $Pd(acac)_2$, $Pd_2(dba)_3$, $Pd(dba)_2$, $Pd(PPh_3)_4$, Pd black and palladium-perovskites, and Pd(0) and Pd(II) catalysts on a solid support or in encapsulated form.

32. The method of claim 31, wherein the metal catalyst is selected from Pd, $PdCl_2$, $Pd(OAc)_2$, $Pd(acac)_2$, $Pd(PPh_3)_4$ and $Pd(dba)_2$.

33. The method of claim 1, further comprising the use of a co-catalyst.

34. The method of claim 33, wherein the co-catalyst is a copper salt, or a cerium salt.

35. The method of claim 1, wherein the metal catalyst is used in amount of about 0.01 mol % to about 20 mol %, about 1 mol % to about 15 mol % or about 5 mol % to about 10 mol %.

36. The method of claim 1, comprising addition of a solvent selected from polar solvents, aprotic polar solvents, aqueous solvents and non-polar organic solvents and mixtures thereof.

* * * * *